(12) United States Patent
Danitz et al.

(10) Patent No.: US 7,615,066 B2
(45) Date of Patent: Nov. 10, 2009

(54) ARTICULATING MECHANISM FOR REMOTE MANIPULATION OF A SURGICAL OR DIAGNOSTIC TOOL

(75) Inventors: David J. Danitz, San Jose, CA (US); Adam C. Gold, New York, NY (US)

(73) Assignee: Novare Surgical Systems, Inc., Cupertino, CA (US)

( * ) Notice: Subject to any disclaimer, the term of this patent is extended or adjusted under 35 U.S.C. 154(b) by 530 days.

(21) Appl. No.: 11/181,445

(22) Filed: Jul. 13, 2005

(65) Prior Publication Data

US 2005/0251112 A1 Nov. 10, 2005

Related U.S. Application Data

(63) Continuation of application No. 10/444,769, filed on May 23, 2003, now Pat. No. 7,090,637.

(51) Int. Cl.
*A61B 17/00* (2006.01)
(52) U.S. Cl. .................. 606/205; 606/207; 606/208; 600/139; 600/141; 600/142; 600/146
(58) Field of Classification Search ............ 600/139, 600/141–142
See application file for complete search history.

(56) References Cited

U.S. PATENT DOCUMENTS

| | | | |
|---|---|---|---|
| 1,820,463 A | 8/1931 | Klein | |
| 3,060,972 A | 10/1962 | Sheldon | |
| 3,071,161 A | 1/1963 | Ulrich | |
| 3,190,286 A | 6/1965 | Stokes | |
| 3,557,780 A | 1/1971 | Sato | |
| 3,605,725 A | 9/1971 | Bentov | |
| 4,466,649 A | 8/1984 | Ozawa | |
| 4,489,826 A | 12/1984 | Dubson | |
| 4,580,551 A | 4/1986 | Siegmund et al. | |
| 4,700,693 A | 10/1987 | Lia et al. | |
| 4,763,669 A | 8/1988 | Jaeger | |
| 4,790,294 A | 12/1988 | Allred et al. | |
| 4,834,761 A | 5/1989 | Walters | |

(Continued)

FOREIGN PATENT DOCUMENTS

EP 0 165 718 12/1985

(Continued)

OTHER PUBLICATIONS

Hegeman et al; U.S. Appl. No. 11/787,543 entitled "Tool with articulation lock," filed Apr. 16, 2007.

(Continued)

*Primary Examiner*—Matthew J Kasztejna
(74) *Attorney, Agent, or Firm*—Shay Glenn LLP

(57) ABSTRACT

The invention provides an articulating mechanism useful, for example, for remote manipulation of various surgical instruments and diagnostic tools within, or to, regions of the body. Movement of segments at the proximal end of the mechanism results in a corresponding, relative movement of segments at the distal end of the mechanism. The proximal and distal segments are connected by a set of cables in such a fashion that each proximal segment forms a discrete pair with a distal segment. This configuration allows each segment pair to move independently of one another and also permits the articulating mechanism to undergo complex movements and adopt complex configurations.

5 Claims, 19 Drawing Sheets

U.S. PATENT DOCUMENTS

| | | |
|---|---|---|
| 4,854,626 A | 8/1989 | Duke |
| 4,880,015 A | 11/1989 | Nierman |
| 4,984,951 A | 1/1991 | Jameson |
| 5,174,276 A | 12/1992 | Crockard |
| 5,257,618 A | 11/1993 | Kondo |
| 5,271,381 A | 12/1993 | Ailinger et al. |
| 5,273,026 A | 12/1993 | Wilk |
| 5,286,228 A | 2/1994 | Lee et al. |
| 5,297,443 A | 3/1994 | Wentz |
| 5,314,424 A | 5/1994 | Nicholas |
| 5,322,064 A | 6/1994 | Lundquist |
| 5,325,845 A | 7/1994 | Adair |
| 5,330,502 A | 7/1994 | Hassler et al. |
| 5,354,162 A | 10/1994 | Burdea et al. |
| 5,381,782 A | 1/1995 | DeLaRama et al. |
| 5,405,344 A | 4/1995 | Williamson et al. |
| 5,425,743 A | 6/1995 | Nicholas |
| 5,441,494 A | 8/1995 | Ortiz |
| 5,454,827 A | 10/1995 | Aust et al. |
| 5,476,479 A | 12/1995 | Green et al. |
| 5,486,154 A * | 1/1996 | Kelleher ................ 600/104 |
| 5,490,819 A | 2/1996 | Nicholas et al. |
| 5,498,256 A * | 3/1996 | Furnish ................ 606/1 |
| 5,520,678 A | 5/1996 | Heckele et al. |
| 5,522,788 A | 6/1996 | Kuzmak |
| 5,549,636 A | 8/1996 | Li |
| 5,570,919 A | 11/1996 | Eusebe |
| 5,599,151 A | 2/1997 | Daum et al. |
| 5,609,601 A | 3/1997 | Kolesa et al. |
| 5,624,398 A | 4/1997 | Smith et al. |
| 5,626,608 A | 5/1997 | Cuny et al. |
| 5,632,432 A | 5/1997 | Schulze et al. |
| 5,643,294 A | 7/1997 | Tovey et al. |
| 5,647,743 A | 7/1997 | Schmitt |
| 5,702,408 A | 12/1997 | Wales et al. |
| 5,704,534 A | 1/1998 | Huitema et al. |
| 5,713,505 A | 2/1998 | Huitema |
| 5,716,352 A | 2/1998 | Viola et al. |
| 5,759,151 A | 6/1998 | Sturges et al. |
| 5,792,164 A | 8/1998 | Lakatos et al. |
| 5,807,376 A | 9/1998 | Viola et al. |
| 5,813,813 A | 9/1998 | Daum et al. |
| 5,823,066 A | 10/1998 | Huitema et al. |
| 5,827,323 A | 10/1998 | Klieman et al. |
| 5,836,960 A | 11/1998 | Kolesa et al. |
| 5,846,183 A | 12/1998 | Chilcoat |
| 5,873,817 A | 2/1999 | Kokish et al. |
| 5,899,425 A | 5/1999 | Corey Jr. et al. |
| 5,916,146 A | 6/1999 | Allotta et al. |
| 5,916,147 A | 6/1999 | Boury |
| 5,921,956 A | 7/1999 | Grinberg et al. |
| 5,938,678 A | 8/1999 | Zirps et al. |
| 5,961,532 A | 10/1999 | Finley et al. |
| 6,019,722 A | 2/2000 | Spence et al. |
| 6,050,996 A | 4/2000 | Schmaltz et al. |
| 6,161,543 A | 12/2000 | Cox et al. |
| 6,250,532 B1 | 6/2001 | Green et al. |
| 6,270,453 B1 | 8/2001 | Sakai |
| 6,446,850 B2 | 9/2002 | Ming-Shun |
| 6,464,704 B2 | 10/2002 | Schmaltz et al. |
| 6,471,641 B2 | 10/2002 | Sakamoto |
| 6,471,696 B1 | 10/2002 | Berube et al. |
| 6,482,149 B1 | 11/2002 | Torii |
| 6,491,626 B1 | 12/2002 | Stone et al. |
| 6,571,042 B1 | 5/2003 | Kordahi |
| 6,626,824 B2 * | 9/2003 | Ruegg et al. ................ 600/104 |
| 6,635,071 B2 | 10/2003 | Boche et al. |
| 6,638,213 B2 | 10/2003 | Ogura et al. |
| 6,638,287 B2 | 10/2003 | Danitz et al. |
| RE38,335 E | 11/2003 | Aust et al. |
| 6,641,528 B2 | 11/2003 | Torii |
| 6,644,532 B2 | 11/2003 | Green et al. |
| 6,666,854 B1 | 12/2003 | Lange |
| 6,669,254 B2 | 12/2003 | Thom et al. |
| 6,676,676 B2 | 1/2004 | Danitz et al. |
| 6,682,541 B1 | 1/2004 | Gifford et al. |
| 6,743,239 B1 | 6/2004 | Kuehn et al. |
| 6,746,443 B1 | 6/2004 | Morley et al. |
| 6,749,560 B1 | 6/2004 | Konstorum et al. |
| 6,764,445 B2 | 7/2004 | Ramans et al. |
| 6,773,327 B1 | 8/2004 | Felice et al. |
| 6,817,972 B2 | 11/2004 | Snow |
| 6,824,548 B2 | 11/2004 | Smith et al. |
| 6,843,794 B2 | 1/2005 | Sixto, Jr. et al. |
| 6,858,005 B2 * | 2/2005 | Ohline et al. ................ 600/141 |
| 6,902,560 B1 | 6/2005 | Morley et al. |
| 6,942,613 B2 | 9/2005 | Ewers et al. |
| 6,945,979 B2 | 9/2005 | Kortenbach et al. |
| 6,960,162 B2 | 11/2005 | Saadat et al. |
| 6,960,163 B2 | 11/2005 | Ewers et al. |
| 6,994,700 B2 | 2/2006 | Elkins et al. |
| 7,138,976 B1 | 11/2006 | Bouzit et al. |
| 2002/0096177 A1 | 7/2002 | Toti et al. |
| 2002/0111604 A1 | 8/2002 | Doyle et al. |
| 2002/0156497 A1 | 10/2002 | Nagase et al. |
| 2002/0161281 A1 | 10/2002 | Jaffe et al. |
| 2002/0177750 A1 | 11/2002 | Pilvisto |
| 2003/0036748 A1 | 2/2003 | Cooper et al. |
| 2003/0050649 A1 | 3/2003 | Brock et al. |
| 2003/0078644 A1 | 4/2003 | Phan |
| 2003/0109898 A1 | 6/2003 | Schwarz et al. |
| 2003/0114838 A1 | 6/2003 | O'Neill et al. |
| 2003/0135204 A1 | 7/2003 | Lee et al. |
| 2003/0149338 A1 | 8/2003 | Francois et al. |
| 2003/0153902 A1 | 8/2003 | Doyle et al. |
| 2003/0229271 A1 | 12/2003 | Briscoe et al. |
| 2003/0233026 A1 | 12/2003 | Saadat et al. |
| 2004/0054322 A1 | 3/2004 | Vargas |
| 2004/0138529 A1 | 7/2004 | Wiltshire et al. |
| 2004/0138700 A1 | 7/2004 | Cooper et al. |
| 2004/0236316 A1 | 11/2004 | Danitz et al. |
| 2005/0090809 A1 | 4/2005 | Cooper et al. |
| 2005/0096694 A1 | 5/2005 | Lee |
| 2005/0107667 A1 | 5/2005 | Danitz et al. |
| 2005/0119527 A1 | 6/2005 | Banik et al. |
| 2005/0273084 A1 | 12/2005 | Hinman et al. |
| 2005/0273085 A1 | 12/2005 | Hinman et al. |
| 2006/0058582 A1 | 3/2006 | Maahs et al. |
| 2006/0094931 A1 | 5/2006 | Danitz et al. |
| 2006/0111209 A1 | 5/2006 | Hinman et al. |
| 2006/0111210 A1 | 5/2006 | Hinman |
| 2006/0111615 A1 | 5/2006 | Danitz et al. |
| 2006/0111616 A1 | 5/2006 | Danitz |

FOREIGN PATENT DOCUMENTS

| | | |
|---|---|---|
| EP | 0 598 618 A2 | 5/1994 |
| EP | 0 836 833 A2 | 4/1998 |
| EP | 0 836 833 A3 | 4/1998 |
| EP | 1 132 041 A2 | 9/2001 |
| EP | 1 395 398 B1 | 3/2004 |
| WO | WO 01/10292 A1 | 2/2001 |
| WO | WO-02/13682 A1 | 2/2002 |
| WO | WO-2004/019769 A1 | 3/2004 |
| WO | WO-2004/105578 A2 | 12/2004 |
| WO | WO-2005/120326 A2 | 12/2005 |
| WO | WO-2005/120326 A3 | 12/2005 |
| WO | WO-2005/120327 A2 | 12/2005 |
| WO | WO-2005/120327 A3 | 12/2005 |
| WO | WO-2006/057699 A1 | 6/2006 |
| WO | WO-2006/057700 A1 | 6/2006 |
| WO | WO-2006/057702 A2 | 6/2006 |

| | | |
|---|---|---|
| WO | WO 2006/073581 A1 | 7/2006 |

OTHER PUBLICATIONS

Hinman, Cameron; U.S. Appl. No. 11/787,607 entitled "Tool with rotation lock," filed Apr. 16, 2007.
Hinman, Cameron; U.S. Appl. No. 11/787,605 entitled "Tool with multi-state ratcheted end effector," filed Apr. 16, 2007.
Hinman et al; U.S. Appl. No. 11/787,599 entitled "Tool with end effector force limiter," filed Apr. 16, 2007.
Hegeman et al; U.S. Appl. No. 11/787,201 entitled "Articulating tool with improved tension member system" filed Apr. 16, 2007.
U.S. Appl. No. 11/344,465, filed on Jan. 30, 2006 for Danitz, 28 pages.
International Search Report mailed Aug. 26, 2005 for PCT Application No. PCT/US04/15944 filed May 21, 2004, 3 pages.
U.S. Appl. No. 10/928,479, filed Aug. 26, 2004 for Hinman et al., 52 pages.
U.S. Appl. No. 10/648,911, filed Sep. 24, 2004 for Danitz et al., 57 pages.
U.S. Appl. No. 10/997,372, filed Nov. 23, 2004 for Danitz et al., 78 pages.
Danitz et al.; U.S. Appl. No. 12/109,333 entitled "Articulating instrument," filed Apr. 24, 2008.

* cited by examiner

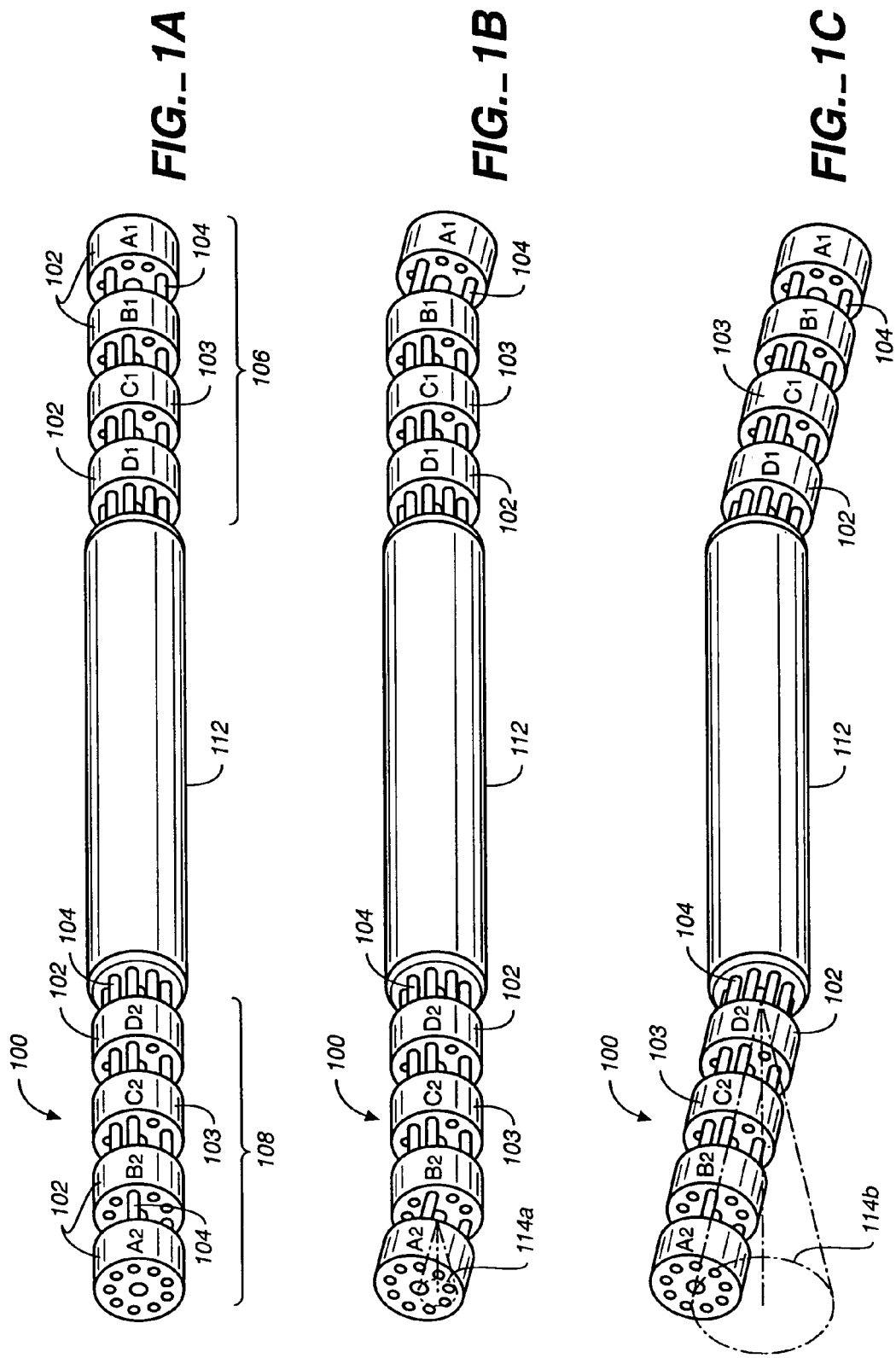

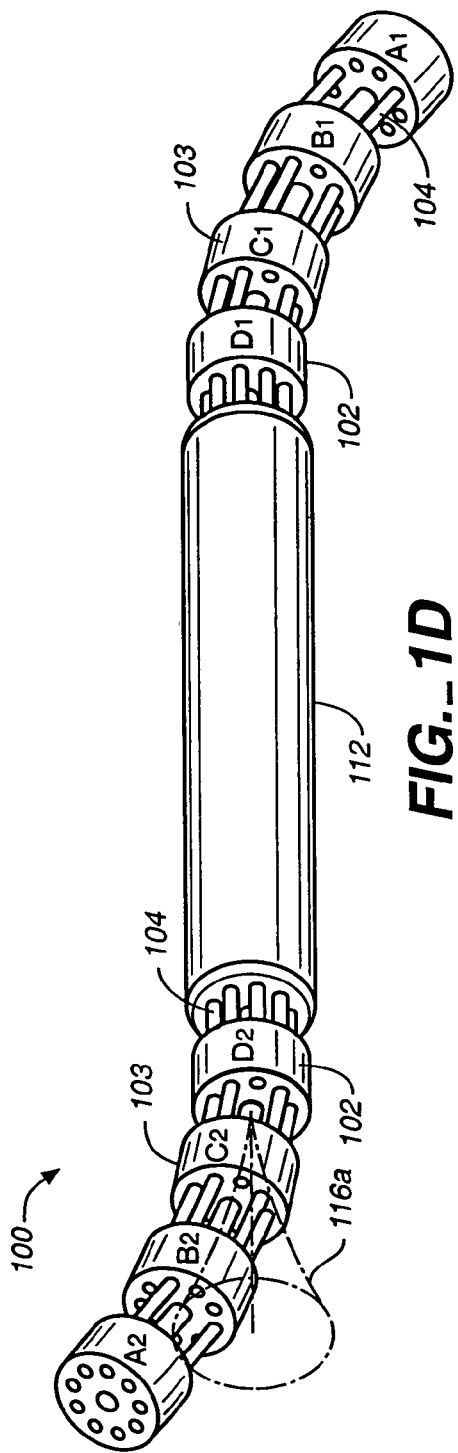
FIG._1D
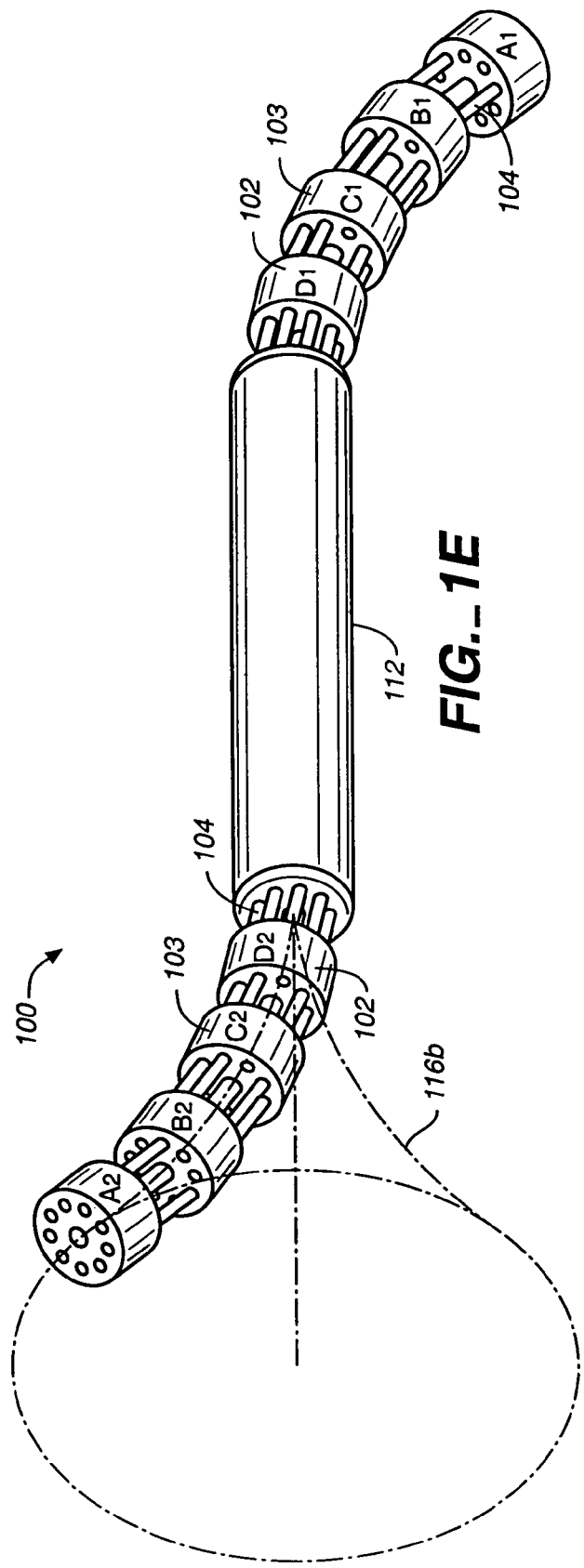
FIG._1E

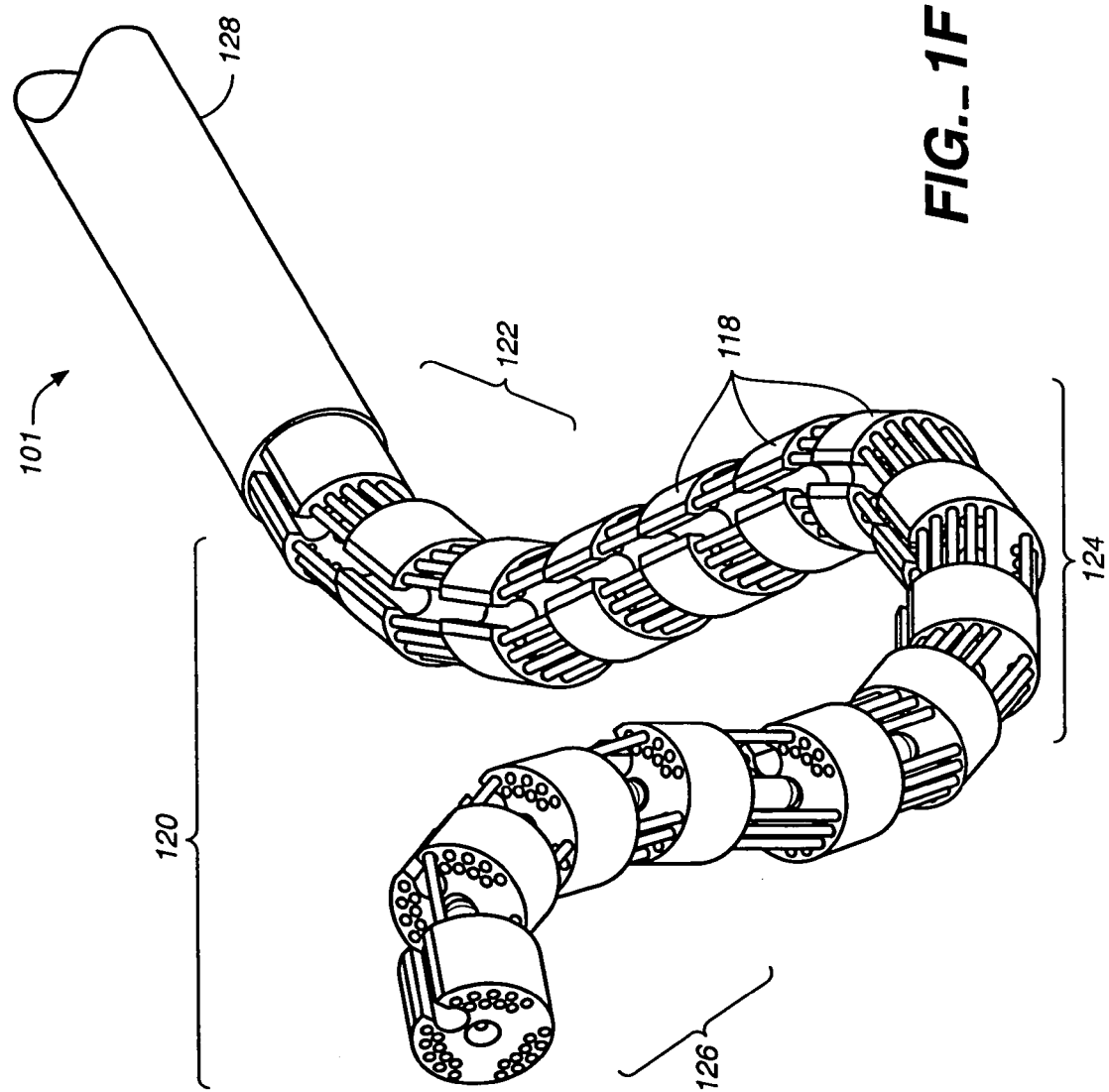
FIG._1F

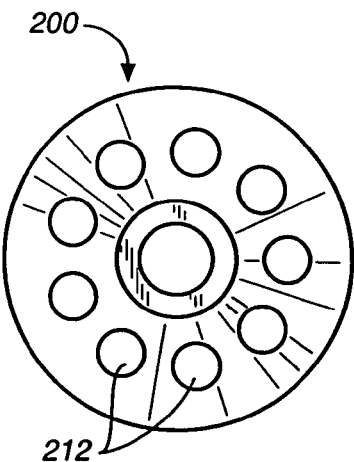
FIG._2A
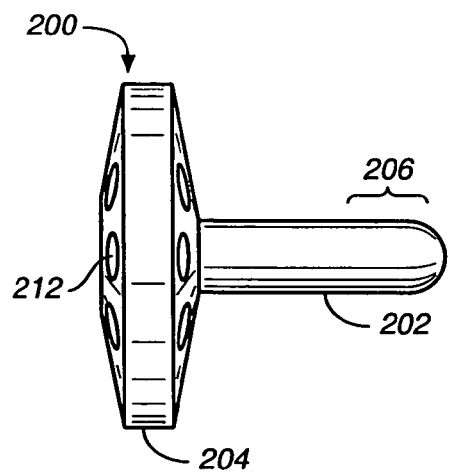
FIG._2B
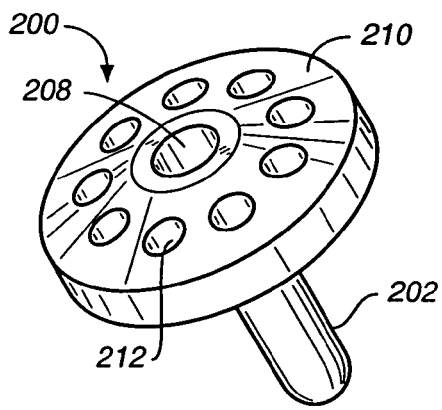
FIG._2C
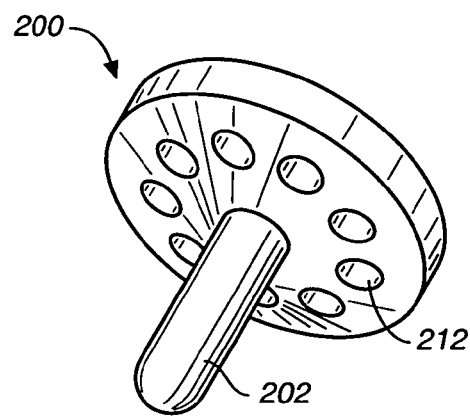
FIG._2D
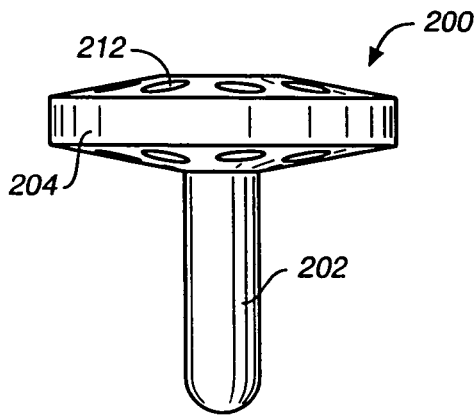
FIG._2E

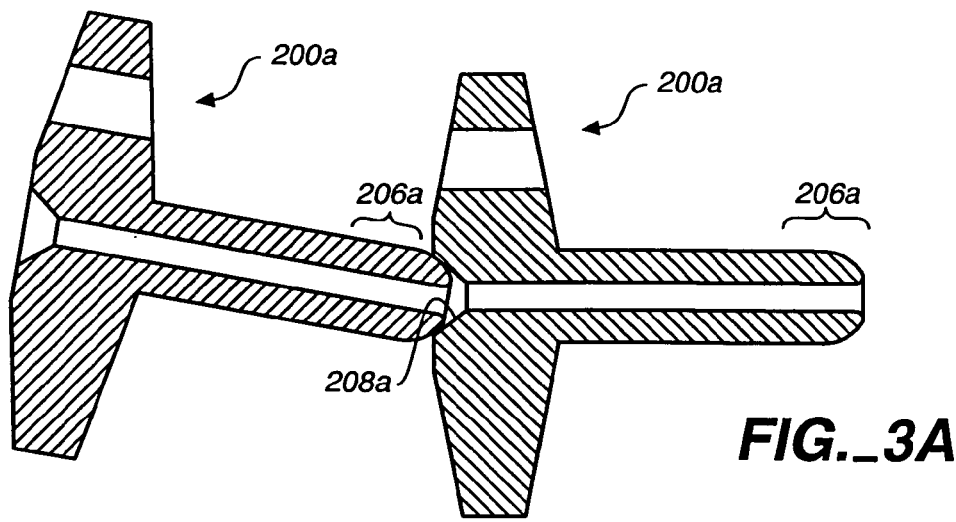
FIG._3A
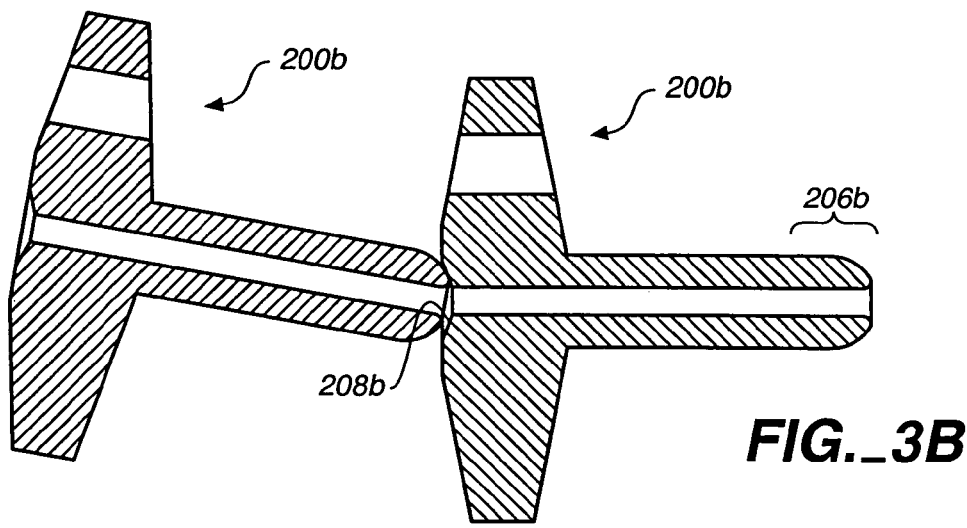
FIG._3B
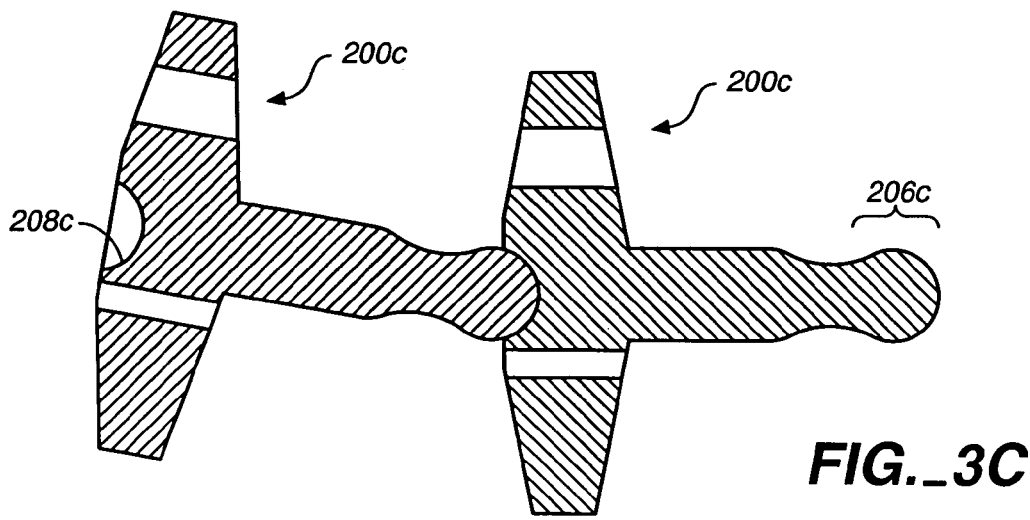
FIG._3C

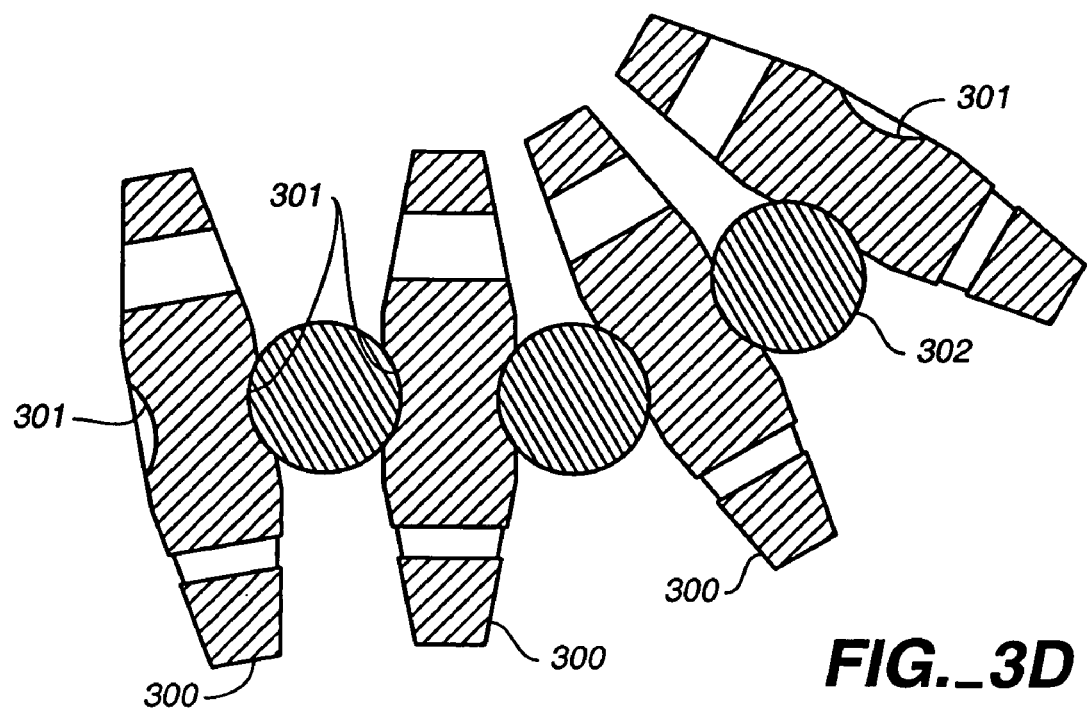
FIG._3D
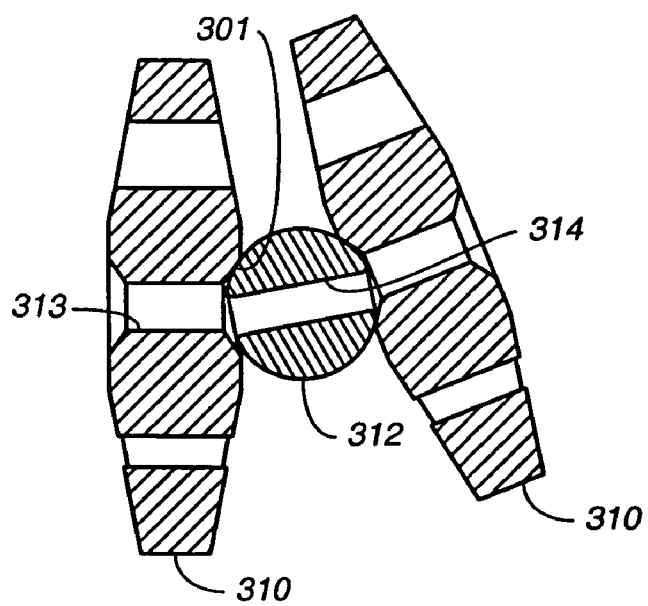
FIG._3E

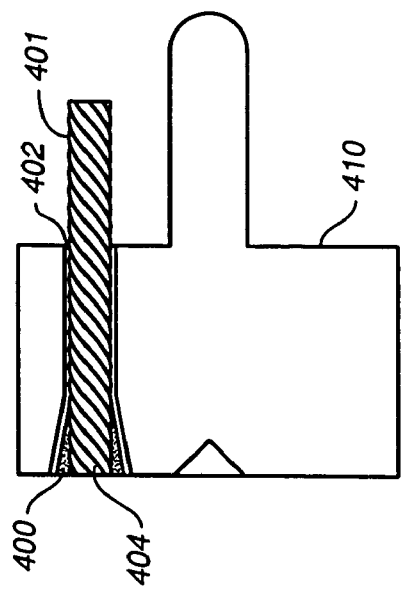
FIG._4C
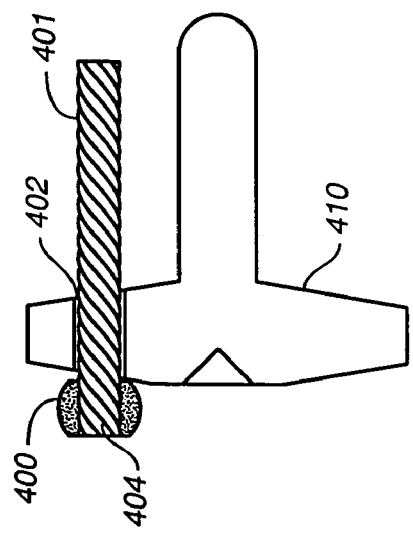
FIG._4B
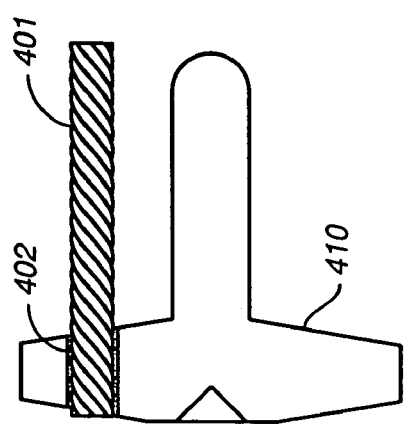
FIG._4A

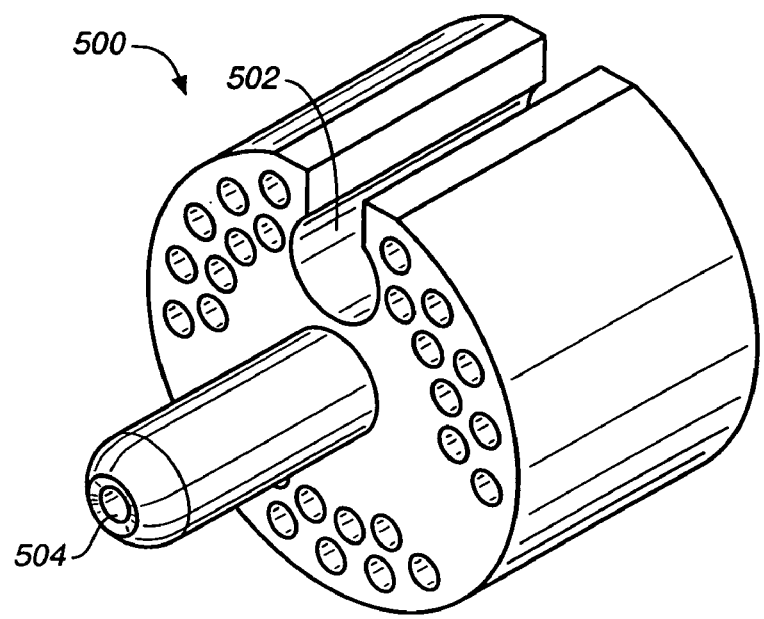
FIG._5A
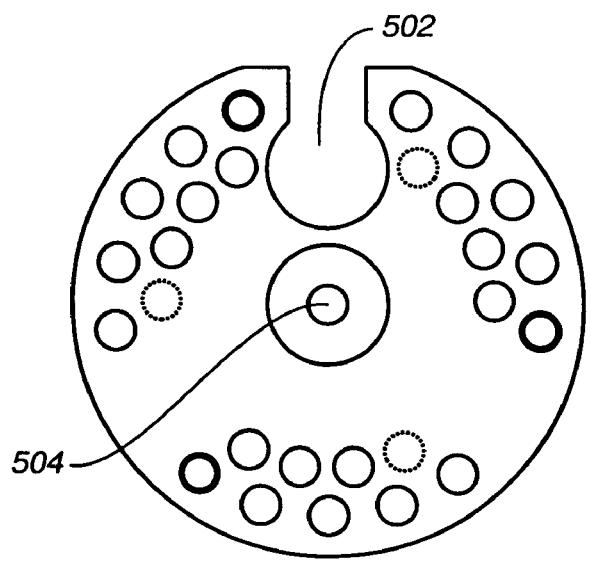
FIG._5B

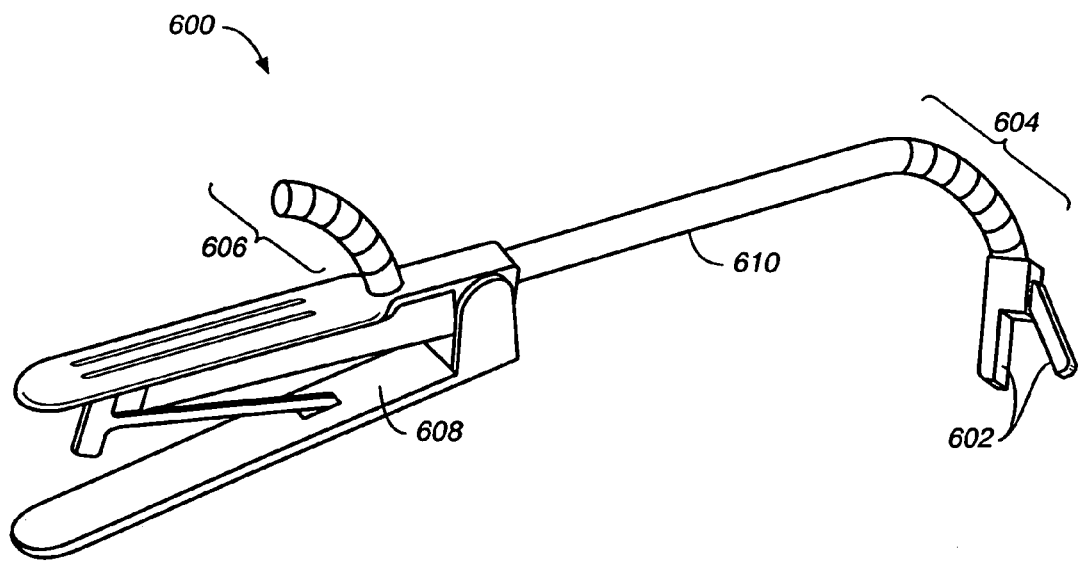
FIG._6A
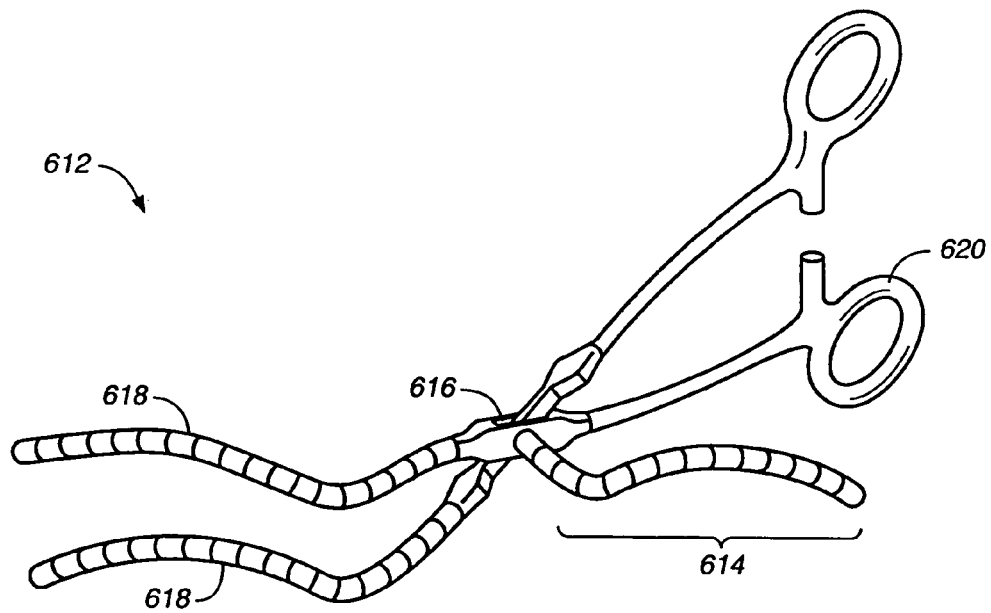
FIG._6B

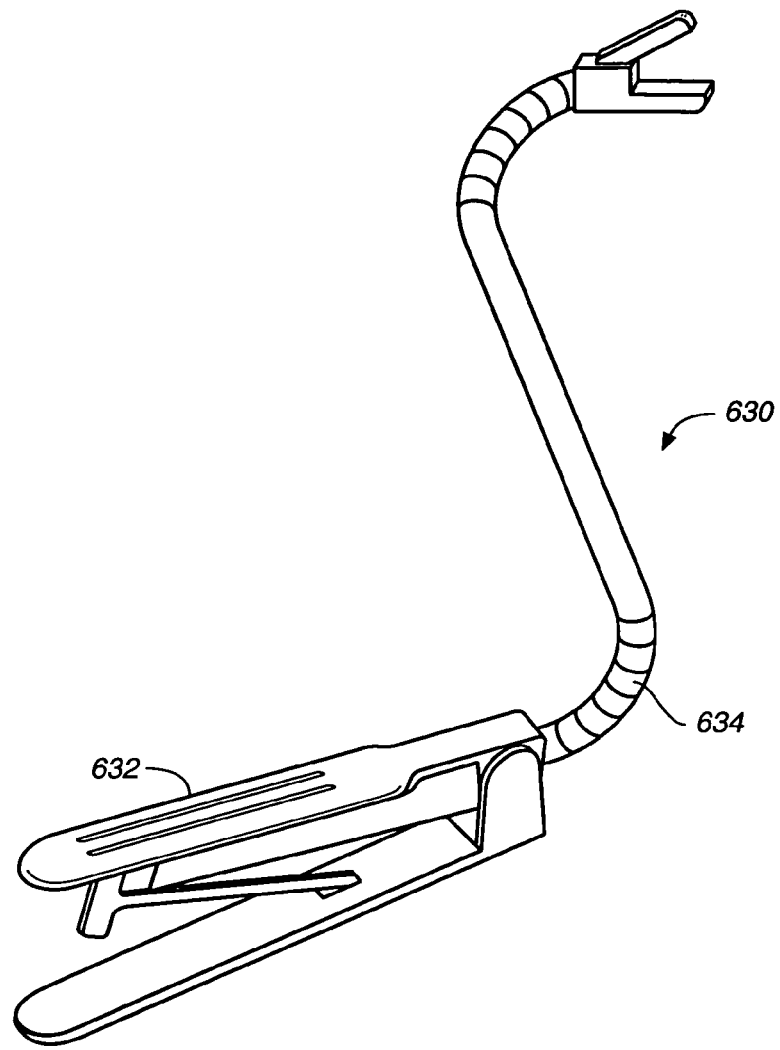
FIG._6C

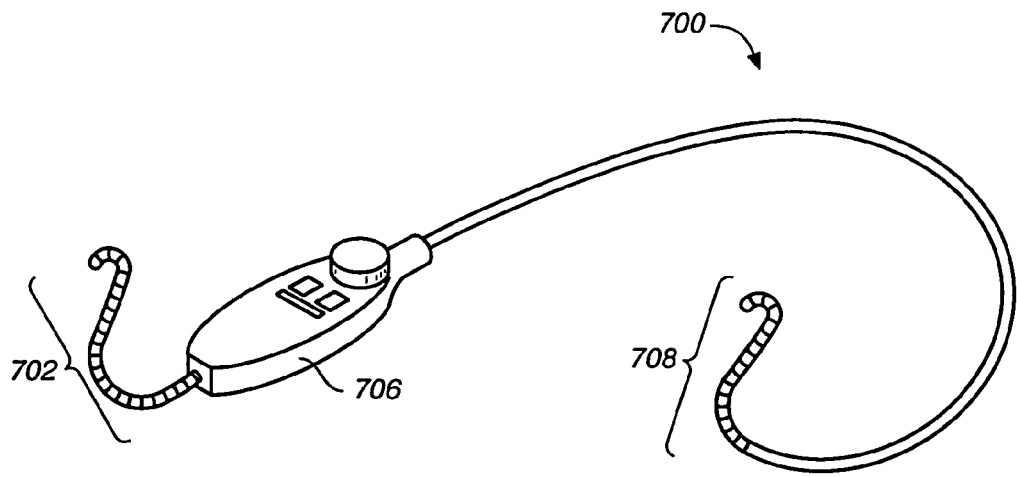
FIG._7
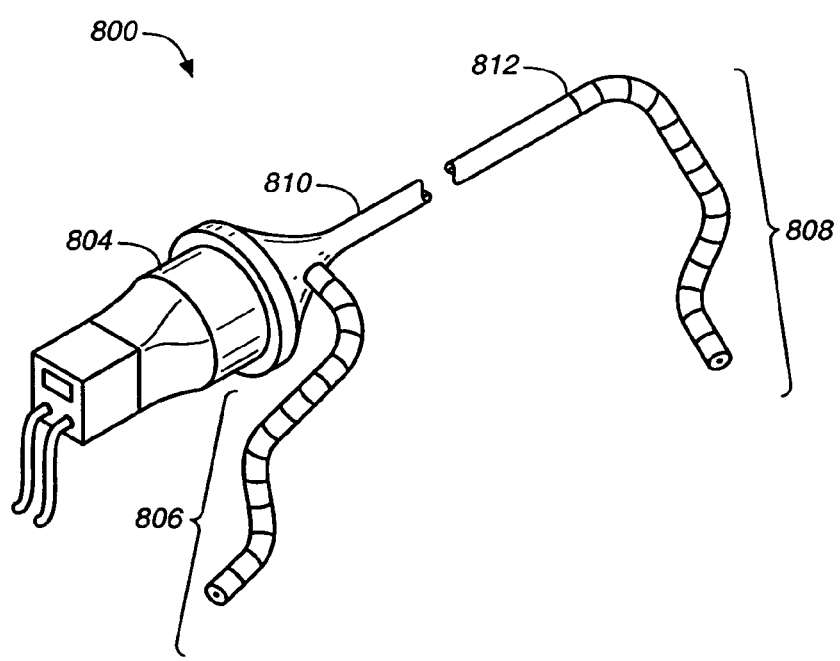
FIG._8

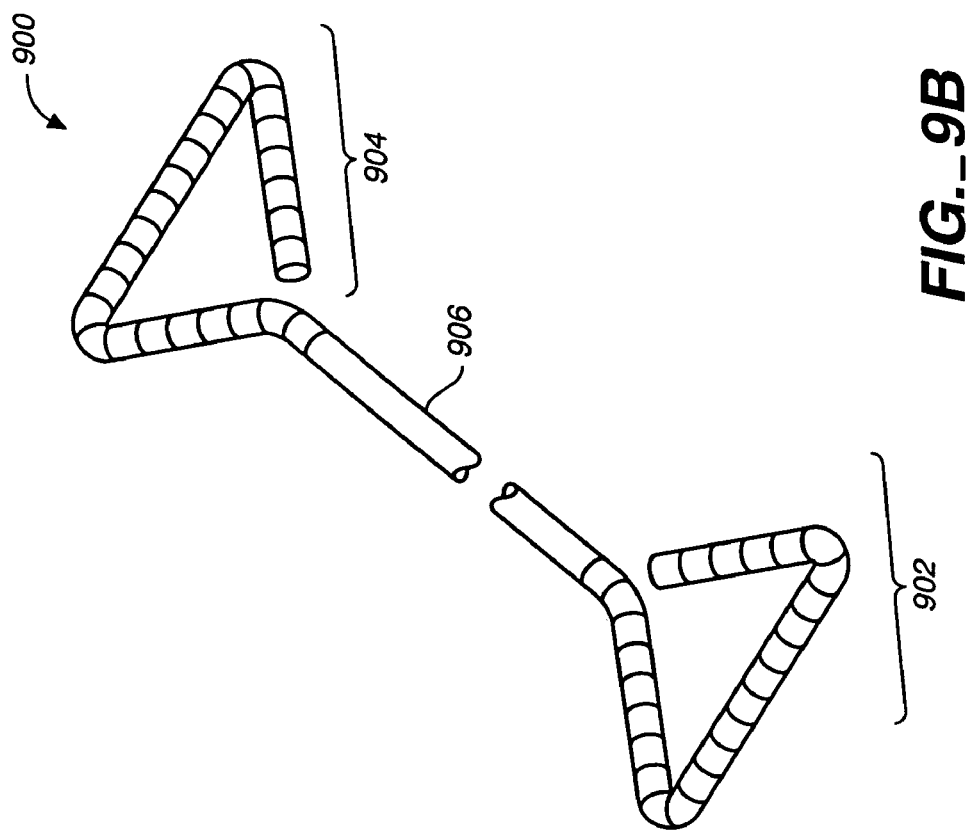
FIG._9B
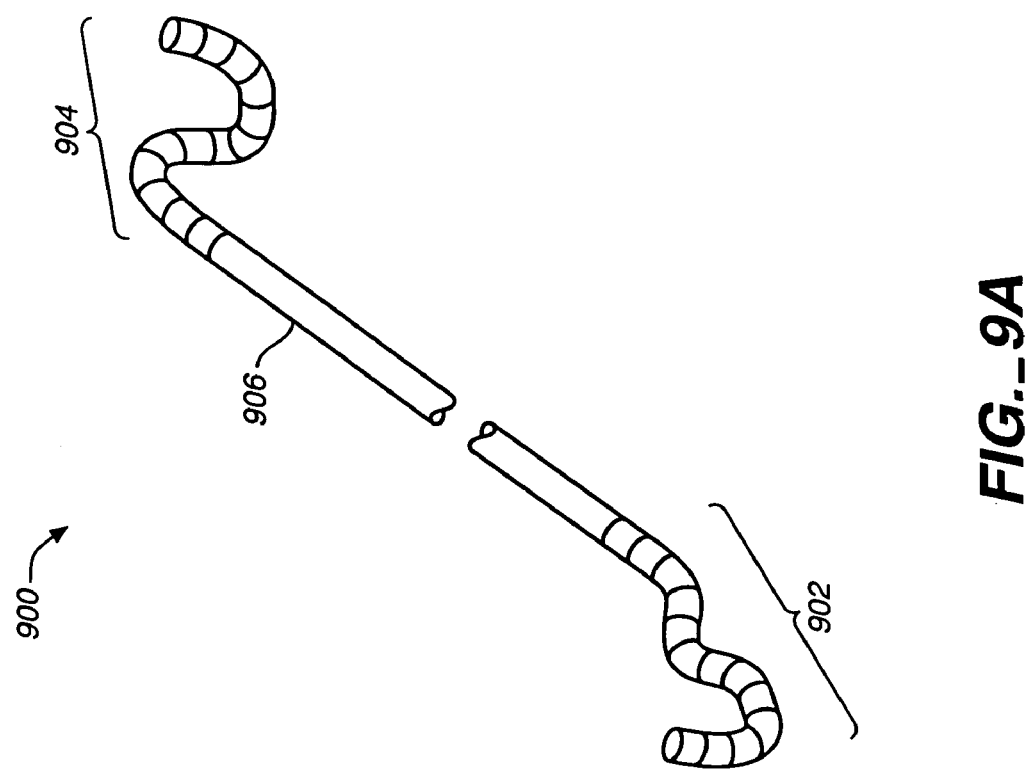
FIG._9A

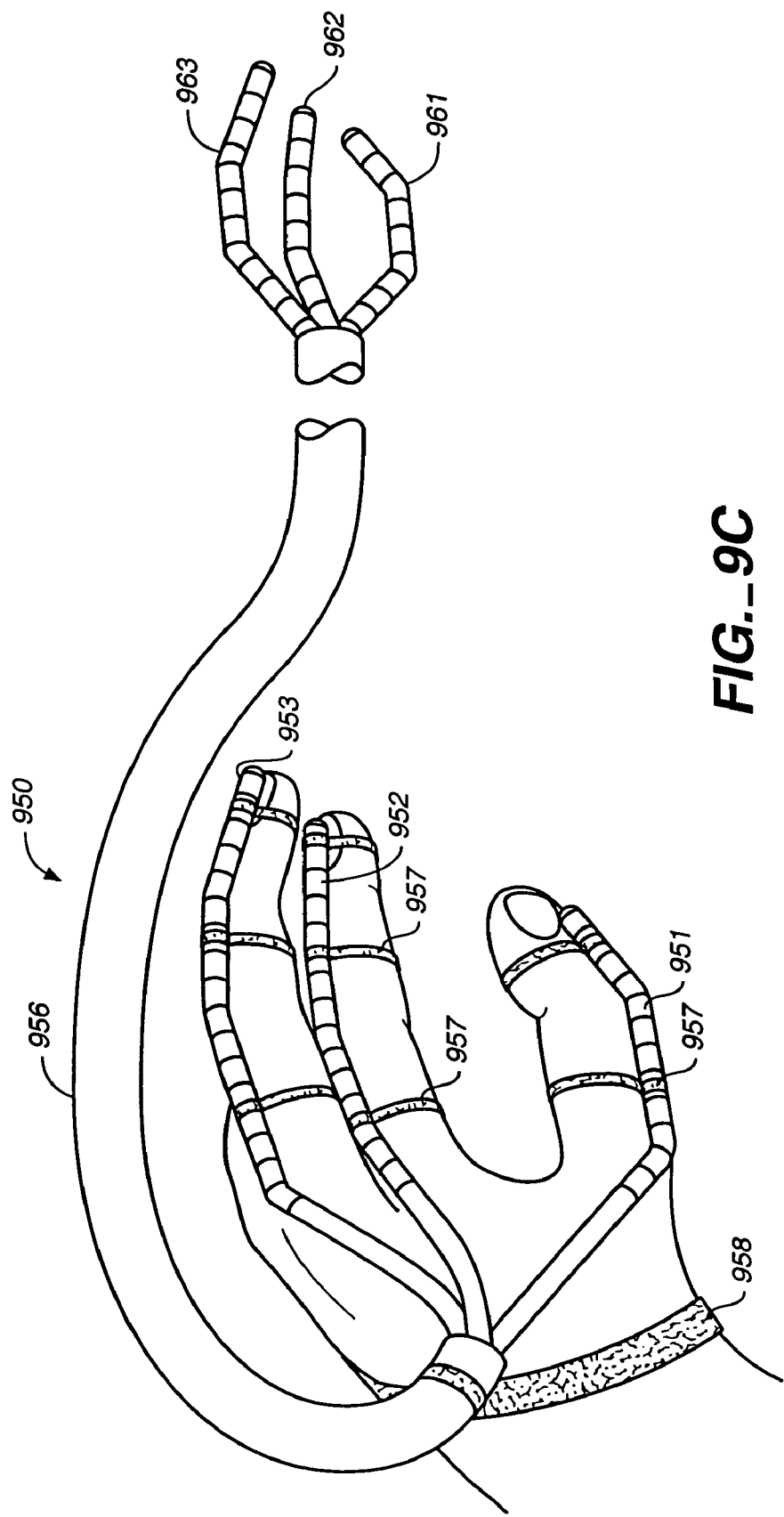
FIG._9C

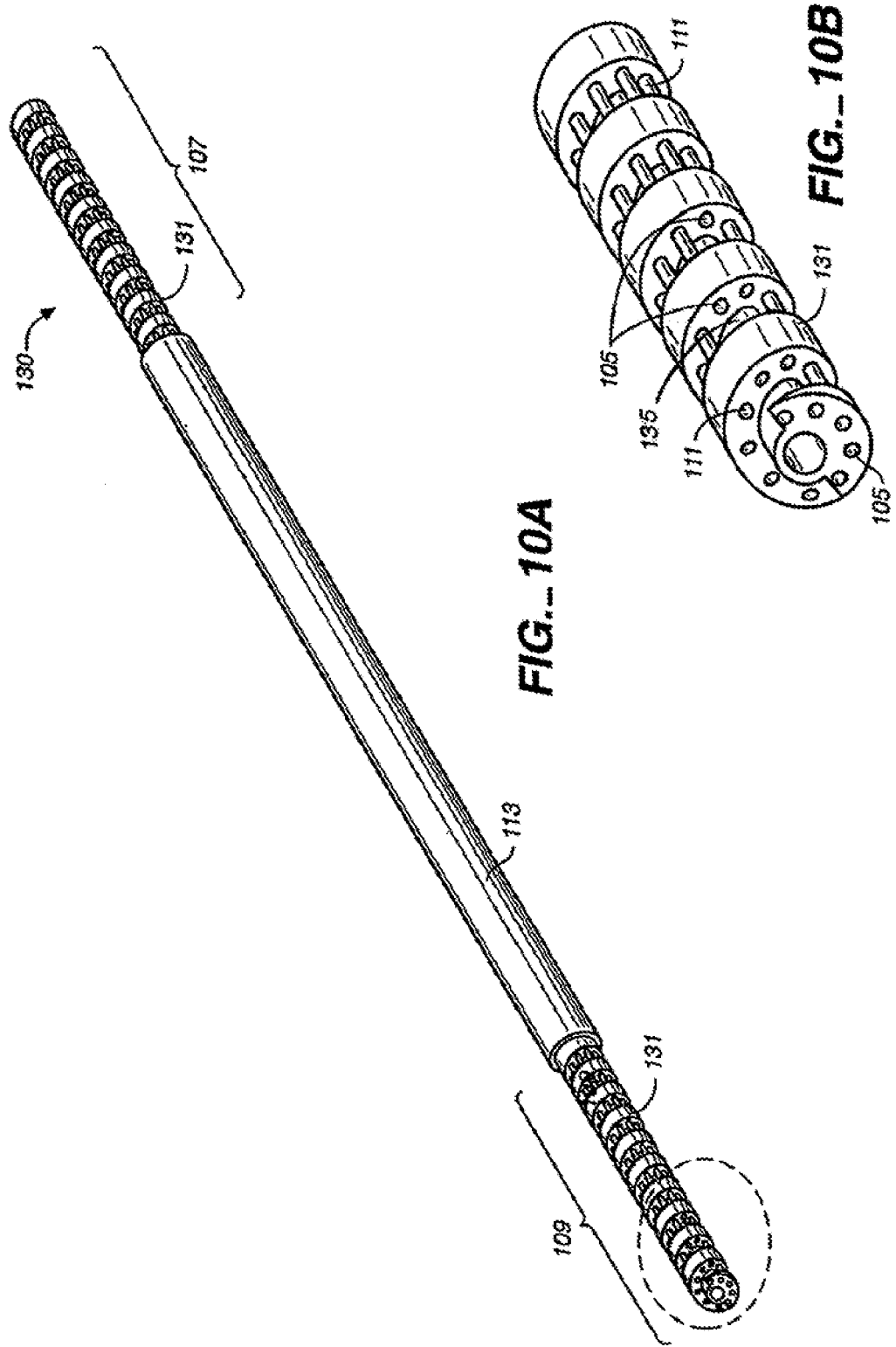

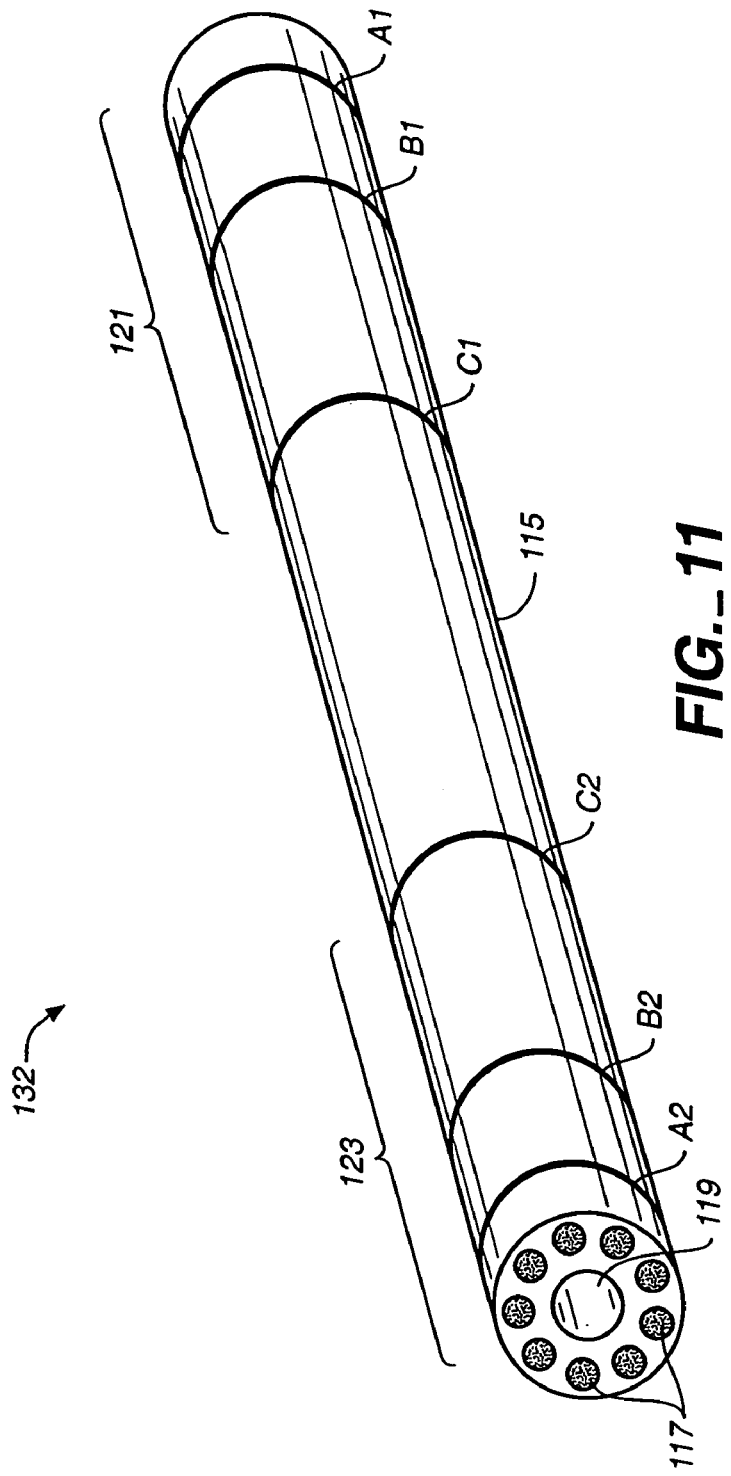
FIG._11

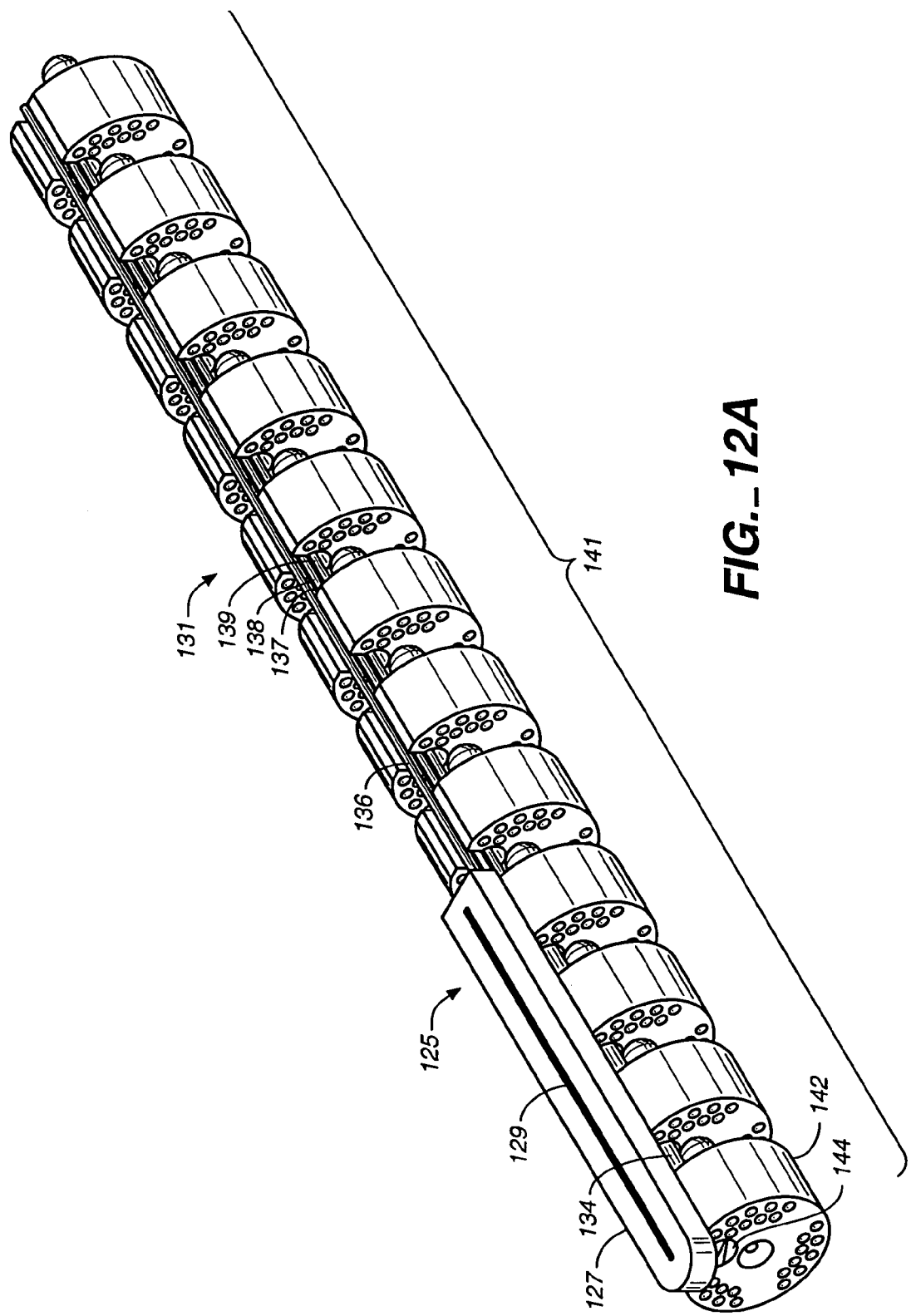
FIG._12A

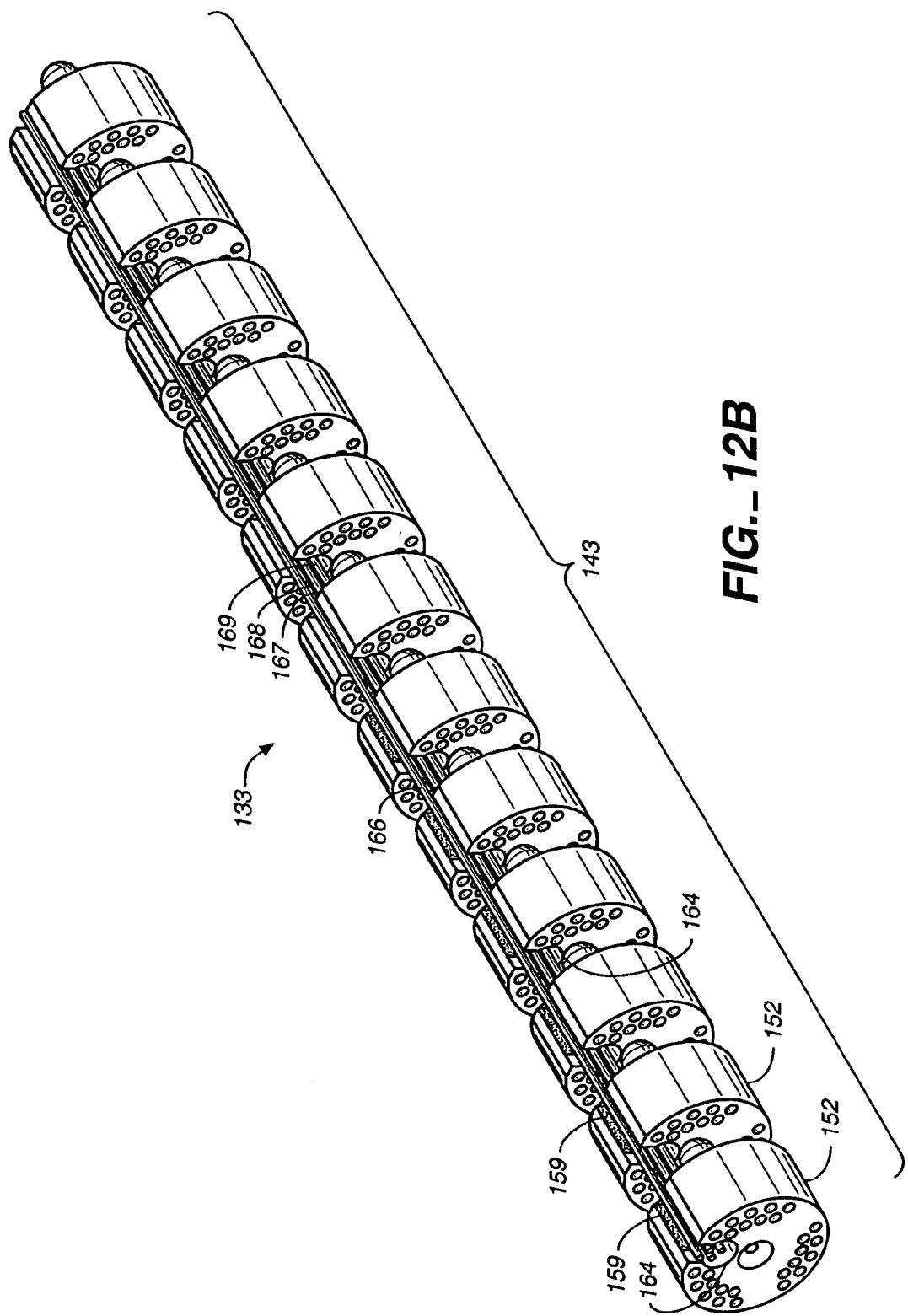
FIG._12B

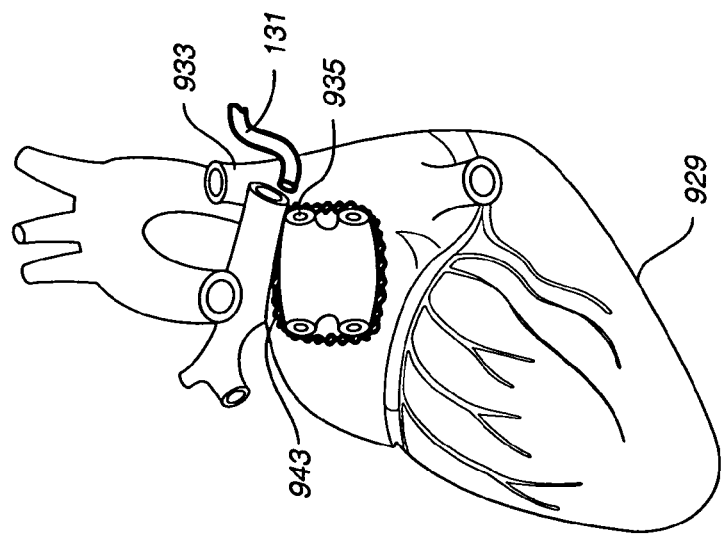
FIG._13C
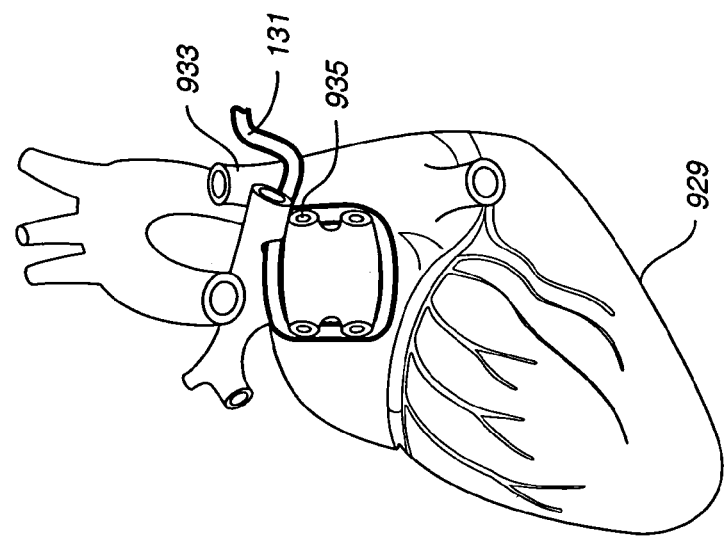
FIG._13B
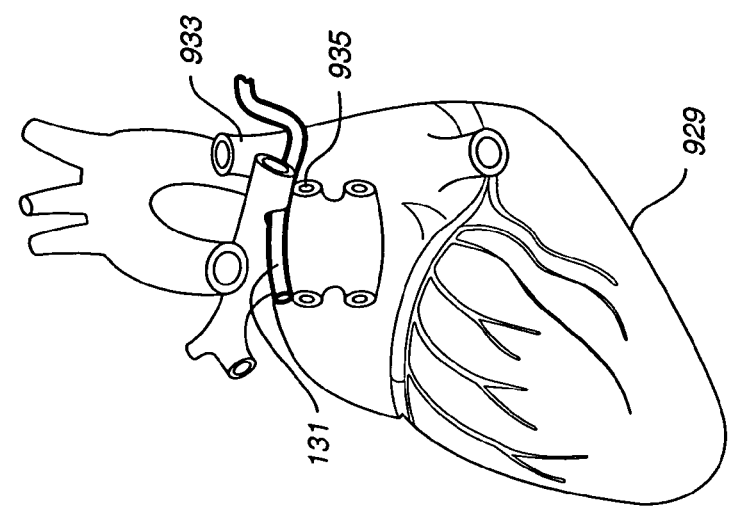
FIG._13A

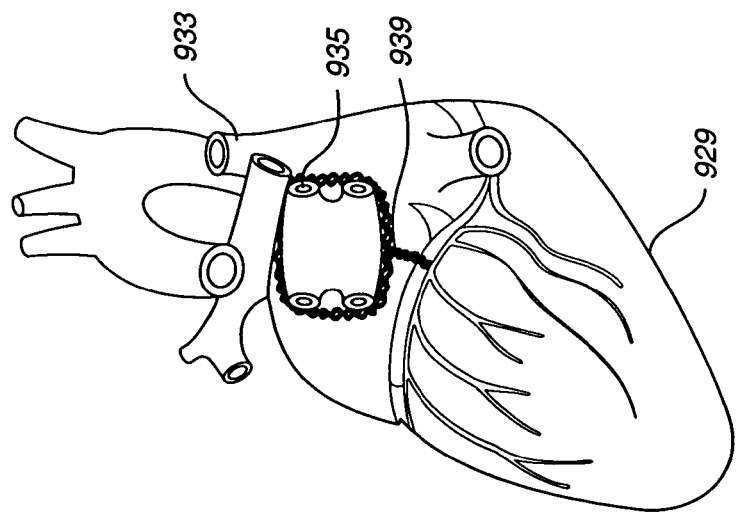
FIG._13F
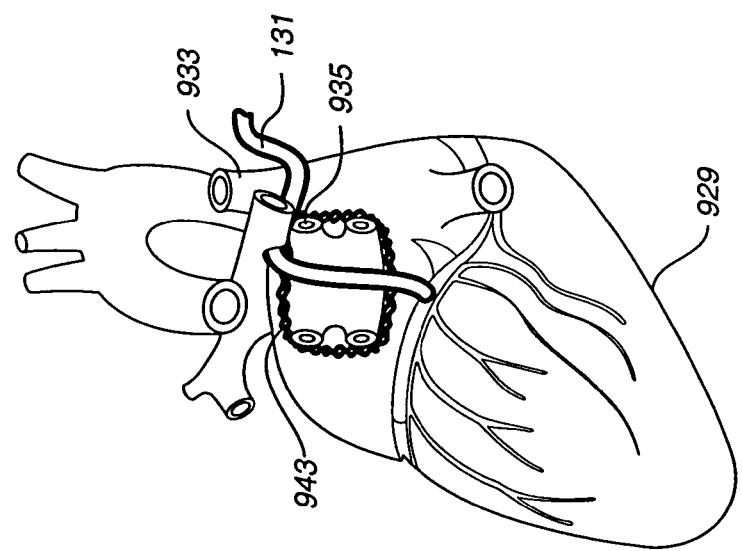
FIG._13E
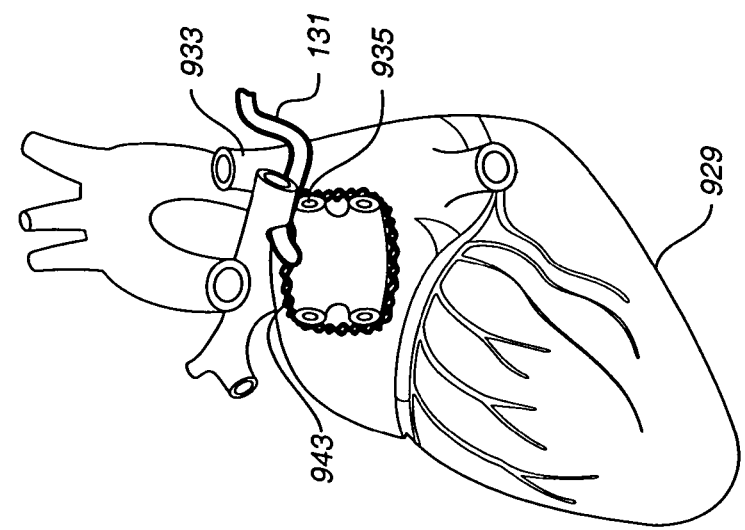
FIG._13D

ARTICULATING MECHANISM FOR REMOTE MANIPULATION OF A SURGICAL OR DIAGNOSTIC TOOL

CROSS REFERENCE TO RELATED APPLICATIONS

This application is a continuation application of U.S. patent application Ser. No. 10/444,769, filed May 23, 2003 now U.S. Pat. No. 7,090,637, which is hereby incorporated by reference in its entirety.

FIELD OF THE INVENTION

This invention relates to articulating mechanisms and applications thereof, including the remote guidance and manipulation of surgical or diagnostic instruments tools.

BACKGROUND OF THE INVENTION

Surgical procedures such as endoscopy and laparoscopy typically employ instruments that are steered within or towards a target organ or tissue from a position outside the body. Examples of endoscopic procedures include sigmoidoscopy, colonoscopy, esophagogastroduodenoscopy, and bronchoscopy. Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues.

Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures.

Steerable catheters are also well known for both diagnostic and therapeutic applications. Similar to endoscopes, such catheters include tips that can be directed in generally limited ranges of motion to navigate a patient's vasculature.

There have been many attempts to design endoscopes and catheters with improved steerability. For example, U.S. Pat. No. 3,557,780 to Sato; U.S. Pat. No. 5,271,381 to Ailinger et al.; U.S. Pat. No. 5,916,146 to Alotta et al.; and U.S. Pat. No. 6,270,453 to Sakai describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), or by a pulley mechanism (Sato).

U.S. Pat. No. 5,916,147 to Boury et al. discloses a steerable catheter having four wires that run within the catheter wall. Each wire terminates at a different part of the catheter. The proximal end of the wires extend loosely from the catheter so that the physician may pull them. The physician is able to shape and thereby steer the catheter by selectively placing the wires under tension.

Although each of the devices described above are remotely steerable, their range of motion is generally limited, at least in part because typically only a single cable set is employed in connecting links or segments of the steerable elements. As such, independent movement at each link or segment is not possible. Rather, the distal links or segments bend together as a unit or units. The steering mechanisms may also be laborious to use, such as in the catheter of Boury et al. where each wire must be separately pulled to shape the catheter. Further, in the case of e.g. endoscopes and steerable catheters that use knob and pulley mechanisms, it requires a significant amount of training to become proficient in maneuvering the device through a patient's anatomy.

Consequently, a device with enhanced remote maneuverability to controllably navigate complex anatomy may allow more efficient and precise advancement and deployment of surgical and diagnostic instruments and tools, as well as help decrease trauma to surrounding tissues, minimize patient discomfort, and decrease operative time and perhaps even patient morbidity during various surgical procedures. It would also be advantageous for such a device to provide a more intuitive and facile user interface to achieve such enhanced maneuverability.

SUMMARY OF THE INVENTION

The present invention provides an articulating mechanism useful for a variety of purposes including but not limited to the remote manipulation of instruments such as surgical or diagnostic instruments or tools, including but not limited to endoscopes, catheters, Doppler flow meters, microphones, probes, retractors, dissectors, staplers, clamps, graspers, scissors or cutters, ablation or cauterizing elements, and the like. The articulating mechanism may be used to steer these instruments within a body region or to a target site within a body region of a patient, and can further be employed to actuate or facilitate actuation of such instruments and tools.

In one variation, the articulating mechanism includes multiple pairs of links, each link of each pair being maintained in a spaced apart relationship relative to the other link of the pair, and multiple sets of cables, with each cable set connecting the links of a discrete pair to one another and terminating at the links of each discrete pair, such that movement of one link of a pair causes corresponding relative movement of the other link of the pair. The relative movement at the distal end of the articulating mechanism corresponds to that at the proximal end.

In another variation, the articulating mechanism includes a continuous flexible member. The continuous flexible member includes multiple pairs of segments, with each segment of each pair being maintained in a spaced apart relationship relative to the other segment of the pair, and multiple sets of cables, with each set connecting the segments of a discrete pair to one another and terminating at the segments of each discrete pair, such that movement of one segment of a pair causes corresponding relative movement of the other segment of the pair. In some instances, the continuous flexible member may be, e.g., a catheter with a plurality of lumens, where each cable set terminates at a different axial location along the length of the catheter. In other instances the continuous flexible member may have a helical arrangement, with each segment corresponding to one turn of the helix. If desired, a flexible linkage may be placed between the helical segments or links.

Variations of the articulating mechanism can also include segments or links that may include a channel for receiving a locking rod that can secure and retain the proximal end of the articulating mechanism in a fixed position. Instead of a rod, a locking sleeve may be fitted over the proximal end of the mechanism to secure and retain the proximal end in a fixed position.

A surgical or diagnostic tool may be attached to, and extend from, the distal end of articulating mechanisms according to the invention, or the articulating mechanisms may be otherwise incorporated into such tools. Examples of surgical or diagnostic tools include, but are not limited to, endoscopes, catheters, Doppler flow meters, microphones, probes, retractors, dissectors, staplers, clamps, graspers, scissors or cutters, and ablation or cauterizing elements.

BRIEF DESCRIPTION OF THE DRAWINGS

FIGS. 1A-1E show perspective views of an articulating mechanism according to one variation of the invention, with multiple pairs of links connected by corresponding sets of cables. FIG. 1A shows the mechanism in its natural configuration. FIGS. 1B to 1E show the mechanism in various states of manipulation.

FIG. 1F is a perspective view of the distal end of an articulating mechanism similar to that of FIG. 1A with the end manipulated into multiple curvatures.

FIGS. 2A-2E depict end, side, and perspective views of a link for use in an articulating mechanism according to another variation of the invention.

FIGS. 3A-3C are cross-sectional views of links similar to those of FIGS. 2A-2E having variously shaped stem portions and corresponding recesses. In FIGS. 3A and 3B, the distal end of the stem portions are convex, while in FIG. 3C it is ball-shaped. The recesses are cone-shaped in FIG. 3A, concave in FIG. 3B, and ball-shaped in FIG. 3C.

FIG. 3D is a cross-sectional view of links for use in an articulating mechanism according to another variation of the invention with spherical elements disposed between the links. FIG. 3E is a cross-sectional view of links and spherical elements similar to those of 3D and which also include a center channel extending through and communicating between the links and spherical elements.

FIGS. 4A-4C are cross-sectional views of links for use in an articulating mechanism according to a variation of the invention showing various modes of connecting cables to the links.

FIGS. 5A and 5B show an individual link for use in an articulating mechanism according to another variation of the invention. FIG. 5A is a perspective view. FIG. 5B is an end view. The depicted link includes lumens and channels for receiving and passing through of cables and other elements.

FIGS. 6A-6C show perspective views of articulating mechanisms associated with a surgical clamp according to variations of the invention.

FIG. 7 is a perspective view of an articulating mechanism associated with a catheter according to a variation of the invention.

FIG. 8 is a perspective view of an articulating mechanism associated with an endoscope according to another variation of the invention.

FIGS. 9A and 9B are perspective views of an articulating mechanism used to remotely form a retractor. In FIG. 9A, the retractor is "u" shaped. In FIG. 9B, the retractor has a triangular retracting surface.

FIG. 9C is a perspective view of an articulating mechanism according to another variation of the invention where the mechanism is attached to the hand of a user.

FIGS. 10A-10B show perspective views of an articulating mechanism according to another variation of the invention having a continuous flexible member that includes helical segments with multiple pairs of such segments connected by corresponding sets of cables. FIG. 10B is an enlarged view, with parts broken away, of the helical segments shown in FIG. 10A.

FIG. 11 is a perspective view of an articulating mechanism according to yet another variation of the invention having a continuous flexible member with a plurality of through lumens with multiple pairs of segments connected by corresponding sets of cables.

FIGS. 12A-12B are perspective views of distal ends of an articulating mechanism according to a further variations of the invention having attached tissue ablation elements.

FIGS. 13A-13F show the distal end of an articulating mechanism according to FIG. 12 being remotely maneuvered to create ablative cardiac lesions.

DETAILED DESCRIPTION OF THE INVENTION

Articulating mechanisms according to the invention generally include multiple pairs of links or segments and multiple sets of cables. The articulating mechanisms may be made from individual, spaced apart segments, i.e., links, or from segments formed from a continuous flexible member. The terms "link" and "segment" as used herein refer to a discrete portion or defined area at one end of the mechanism that corresponds to another discrete portion or defined area at the opposite end of the mechanism. In any event, the articulating mechanism will include a plurality of links or segments that are members of discrete pairs. The links or segments form a proximal end and a distal end, with one link or segment of each pair being situated at the proximal end, and the other link or segment at the distal end. As further described below, links or segments formed from a continuous flexible member may be in the form of, e.g., a continuous tube, or may be situated in, e.g., a helical arrangement, where each segment corresponds to one turn of the helix.

Each cable set connects the links or segments of a discrete pair to one another so that movement of one link or segment of a pair causes a corresponding movement of the other link or segment in the pair. The ability to manipulate individual links allows for the mechanism to readily form complex three-dimensional configurations and geometries as is further detailed herein. With conventional articulating devices that rely on cable sets or wires, it is difficult to obtain such complex geometries because such devices are typically designed such that the steering cables or wires pass through each segment and terminate in a distal-most segment. Thus, all the segments bend together in a coordinated response to movement of the wire or cable set, typically in a curved, or arcuate fashion. For example, the device described by Alotta et al. in U.S. Pat. No. 5,916,146 has such a configuration.

For purposes of illustration, articulating mechanisms of the invention will be described in the context of use for the remote guidance, manipulation and/or actuation of surgical or diagnostic tools and instruments in remote accessed regions of the body. The terms "instrument" and "tool" are herein used interchangeably and refer to devices that are usually handled by a user to accomplish a specific purpose. The term "region" as used herein refers to any solid organ (e.g., liver, kidney, brain, heart) or hollow organ (e.g., esophagus, intestines, stomach, bladder), any solid or luminal (e.g., blood vessels or ducts) tissue, or any body cavity (e.g., sinus, pleural or peritoneal space), in their diseased or nondiseased state. Other applications of the articulating mechanism besides surgical or diagnostic applications are also contemplated and will be apparent to one of skill in the art. These include, without limitation, industrial uses, such as for the navigation of a tool, probe, sensor, etc. into a constricted space, or for precise manipulation of a tool remotely. Other uses include applications where remote manipulation of complex geometries is also desirable. These include uses in recreation or entertainment, such as toys or games, e.g, for remote manipulations of puppets, dolls, figurines, and the like.

Turning to the variation shown in FIG. 1A, articulating mechanism 100 includes a plurality of links 102 that form a proximal end 106 and a distal end 108. Links $A_1$ and $A_2$, $B_1$ and $B_2$, and $D_1$ and $D_2$, respectively, are members of a discrete pair, and one link of a pair is at the proximal end 106 while the other is at the distal end 108. Links $C_1$ and $C_2$ are spacer links, as will be described in greater detail herein. The proximal links ($A_1$, $B_1$, $D_1$) are connected to the distal links ($A_2$, $B_2$, $D_2$) by cables 104. A spacer element 112 is disposed between the proximal end 106 and the distal end 108 to separate the proximal links from the distal links and to maintain them in a spaced apart relationship. The spacer element 112 may be of any length appropriate to the intended application, and is typically hollow so that it may accommodate all the cables 104 that connect the link pairs, as well as additional cables, wires, fiberoptics or other like elements associated with a desired tool or instrument used in conjunction with the mechanism.

The links may be of any size and shape, as the purpose dictates, but their form usually depends on such factors as patient age, anatomy of the region of interest, intended application, and surgeon preference. Links 102, for example, are generally cylindrical, and include channels for passage of the cables that connect the link pairs as well as additional cables, wires, fiberoptics or other like elements associated with a desired tool or instrument used in conjunction with the mechanism. The channel diameters are usually slightly larger than the cable diameters, creating a slip fit. Further, the links may also include one or more channels for receiving elements of attachable surgical instruments or diagnostic tools or for passage of cables that actuate them. The links may typically have a diameter from about 0.5 mm to about 15 mm or more depending on the application. For endoscopic applications, representative diameters may range from about 2 mm to about 3 mm for small endoscopic instruments, about 5 mm to about 7 mm for mid-sized endoscopic instruments, and about 10 mm to about 15 mm for large endoscopic instruments. For catheter applications, the diameter may range from about 1 mm to about 5 mm. Overall length of the links will vary, usually depending on the bend radius desired between links.

In the variation shown in FIGS. 2A-2E, links 200 are generally cylindrical and also include stem portion 202. Links 200 may be aligned so that the distal end 206 of stem portion 202 engages a corresponding recess 208 formed in the surface 210 of an adjacent segment. The distal end of the stem portion may be of various shapes. For example, links 200a and 200b have convex ends 206a and 206b, respectively, (FIGS. 3A, 3B) whereas link 200c has a ball-shaped end 206c (FIG. 3C). Similarly, the corresponding recesses may be of variouis corresponding shapes, e.g., concave as in recesses 206b and 206c (FIGS. 3B and 3C) or cone-shaped as in recess 206a (FIG. 3A), so long as it permits each link to engage one another and does not restrict the required range of motion for the articulating mechanism.

The stem portion 202 may typically have a length between about 0.5 mm to greater than about 15 mm and a diameter between about 0.5 mm to about 2.5 mm. For endoscopic applications, the stem diameter may range from about 1 mm to about 1.5 mm. Links 200 also include a plurality of channels 212 for passage of the cables that connect the link pairs, as shown in FIGS. 2A-2E. Link 500, as shown in FIG. 5, is designed with an attachment channel 502 that communicates with the segment exterior and is located toward the periphery of the segment, for mounting other elements, e.g., energy sources (for ablation or coagulation) or fiberoptics, or flexible endosocopes, at the distal end of the articulating mechanism. More than one link or segment may include an attachment channel so that the attachment channel may extend from the distal end to the proximal end of the mechanism. Cables, wires, fiberoptics, flexible endoscopes and the like, may also be run through a central channel 504 if desired.

The links or segments may be made from any biocompatible material including, but not limited to, stainless steel; titanium; tantalum; and any of their alloys; and polymers, e.g., polyethylene or copolymers thereof, polyethylene terephthalate or copolymers thereof, nylon, silicone, polyurethanes, fluoropolymers, poly (vinylchloride); and combinations thereof.

A lubricious coating may be placed on the links or segments if desired to facilitate advancement of the articulating mechanism. The lubricious coating may include hydrophilic polymers such as polyvinylpyrrolidone, fluoropolymers such as tetrafluoroethylene, or silicones.

A radioopaque marker may also be included on one or more segments to indicate the location of the articulating mechanism upon radiographic imaging. Usually, the marker will be detected by fluoroscopy.

Each link or segment at the proximal end of the articulating mechanism is connected to its corresponding link or segment at the distal end by two or more cables. Each cable set may be made up of at least two cables. As noted, movement of one pair is controlled by its corresponding cable set and is independent of any other pair. In certain variations, for example, a cable set will include three cables spaced 120 degrees apart. By using a set of three cables to connect each link or segment pair, each link or segment pair can be manipulated or moved in three degrees of freedom, independently of any other pairs. By combining a plurality of link or segment pairs, multiple degrees of freedom are achieved, allowing the articulating mechanism to be shaped into various complex configurations. For example, the variation shown in FIG. 1F has a total of nine link pairs each independently connected by sets of three cables each, for possible motion in 27 degrees of freedom. Such multiple degrees of freedom are not available in typical conventional mechanisms where only a single set of cables is employed to manipulate the links.

Cable diameters vary according to the application, and may range from about 0.15 mm to about 3 mm. For catheter applications, a representative diameter may range from about 0.15 mm to about 0.75 mm. For endoscopic applications, a representative diameter may range from about 0.5 mm to about 3 mm.

Cable flexibility may be varied, for instance, by the type and weave of cable materials or by physical or chemical treatments. Usually, cable stiffness or flexibility will be modified according to that required by the intended application of the articulating mechanism. The cables may be individual or multi-stranded wires made from material, including but not limited to biocompatible materials such as nickel-titanium alloy, stainless steel or any of its alloys, superelastic alloys, carbon fibers, polymers, e.g., poly (vinylchloride), polyoxyethylene, polyethylene terephthalate and other polyesters, polyolefin, polypropylene, and copolymers thereof; nylon; silk; and combinations thereof, or other suitable materials known in the art.

Referring to FIG. 1A, cables fixed to a proximal link travel through a spacer element 112 to connect with a corresponding distal link of the pair. As shown in FIGS. 1B-1E, movement of proximal links results in inverted, reciprocal movement of distal links. In other variation, the cables can be twisted or rotated 180 degrees while running through the spacer element 112 so that the reciprocal movement at the distal end 108 is mirrored. The articulating mechanisms of this invention may be configured to include cables twisted in any amount between 0 degrees to 360 degrees to provide for 360 degree range of reciprocal motion.

The cables may be affixed to the links of a pair according to ways known in the art, such as by using an adhesive or by brazing, soldering, welding, and the like. FIG. 4a shows cable 401 affixed within channel 402 of link 410 in such manner. In another variation depicted in FIG. 4B, a cable terminator 400 is mounted, e.g. crimped, brazed, welded, or glued, onto cable end 404 to prevent its slippage through the channel 402. In a further variation, as shown in FIG. 4C, the cable terminators 400 are swaged to form a chamfer within channel 402 so that a friction fit is made between the cable end 404 and cable terminators 400.

FIGS. 10A and 10B show a variation of the invention. Rather than individual links or segments, the segments of articulating mechanism 130 are formed from a continuous flexible member, depicted as an elongated coil. Each turn of the coil is a helical segment 131 of the articulating mechanism. An example of a flexible linkage 135 positioned between adjacent segments 131 is shown in FIG. 10B. The segments 131 are of a thickness that allow channels 105 to run through them, parallel to the axis of the coil. The helical segments at the proximal end 107 form discrete pairs with segments at the distal end 109. Each segment pair is connected by its own set of cables 111. A spacer element 113 is also disposed between the proximal end 107 and distal end 109 to separate the proximal segments from the distal segments. The cables can be affixed to the helical segments as previously described.

In yet another variation of the invention, as shown in FIG. 11, articulating mechanism 132 is formed of a continuous tube 115 having multiple lumens 117 running through the entire length of the tube. The continuous tube 115 may also optionally include central lumen 119. Cable sets may run the length of the tube and be anchored at varying corresponding axial locations at the proximal and distal ends with, e.g., an epoxy, or run between each segment of a pair and be anchored at or in the vicinity of each segment at the proximal and distal end. For example, at the mechanism proximal end 121, one cable set may be anchored at $A_1$, another at $B_1$, and another at $C_1$. Each cable set would then be anchored at a corresponding location at the mechanism distal end 123, e.g., at locations $A_2$, $B_2$, and $C_2$.

The cables that run between segment pairs may be precisely cut to a certain length, but if desired, may be cut to approximate that length. One method of placing the cables involves advancing the cables through the lumens using a pusher. A visual marker or tactile stop on the pusher would indicate how far to advance the pusher. After the pusher is removed, a needle may be introduced into each lumen to deposit epoxy from, e.g., a syringe exterior to the tube, at each cable end. In another method, which for example can be used with cable sets running the entire length of the tube, the needle may be directed to puncture through the wall of the tube at or near each desired cable attachment point to deliver epoxy to the cable at the desired point, thereby attaching each cable to each corresponding segment pair.

Although the many of the articulating mechanisms have been illustrated in the above figures as having only eight links (four pairs), this is solely for the illustrative purpose of indicating the relationship of the individual device components to one another. Any number of links and link pairs may be employed, depending on such factors as the intended body region of use and desired length of the articulating mechanism. For example, articulating mechanism 101 of FIG. 1F has nine link pairs.

Spacer links, i.e., links not connected by discrete sets of cables (e.g., $C_1$ and $C_2$ in FIGS. 1A-1E), may also be included in the articulating mechanisms. These links can be inserted between active links at either the proximal or distal ends or both, and act as passive links that are not independently actuatable, but do allow for pass through of cable sets to neighboring active links. Spacer links can be desirable for providing additional length to the proximal or distal end. In addition the inclusion of spacer links at one end of the mechanism allows for the proportional scaling of movement or motion of the corresponding other end. For example, the inclusion of spacer links at the distal end would require a more exaggerated movement by the user at the proximal end to achieve to achieve the desired motion at the distal end. This could be advantageous in situations where fine, delicate controlled movements were desired, such as, for example, situations where there is a risk that a user may not possess the necessary dexterity to perform the desired procedure absent such proportional scaling of the distal end movement or motion. Alternatively, spacer links could be provided on the proximal end, in which case the degree of distal end movements would be proportionally greater than those of the proximal end, which may also be desirable for particular applications.

As noted, the articulating mechanisms of this invention may be used to direct a surgical or diagnostic instrument tool within a body region or to a target site within a body region of a patient either in its native, straight configuration, or after undergoing various manipulations at its proximal end from a location outside the patient. After appropriate insertion, movement of the proximal end of the mechanism, results in reciprocal movement at the distal end. Further, the resulting directional movement of the distal end can be inverted, mirrored or otherwise, depending on the degree of rotation of the proximal end relative to the distal end. Also, the proximal end provides for a user interface to control the steering and manipulation of the distal end that is convenient and easy to use relative to other conventional steering mechanisms that rely on e.g., pulleys or knobs to control steering wires. This user interface allows for example a user to readily visualize the shape and directional movement of distal end of the mechanism that is located e.g. within a patient based on the manipulated shape of the externally positioned proximal end user interface.

Complex movements, including up, down, right, left, oblique, and rotational movements, may be accomplished due to the formation of multiple pairs of segments or links connected by discrete cable sets, as described above. For example, in the variation shown in FIG. 1B, the most distal link at the distal end, $A_2$, may be actuated, while all other links remain stationary by actuation of the most distal link at the proximal end, $A_1$. For illustrative purposes, the distal-most link is shown to be rotated to form a right circular cone 114a, the base diameter of which increases with such factors as increased length of stem portions, enhanced cable flexibility, and addition of spacer links 103 (e.g., Co) in addition to the other links.

As shown in FIG. 1C, the most proximal link at the distal end, $D_2$, is actuated while all other links remain stationary by actuating only the most proximal link at the proximal end, link $D_1$. Upon rotation, the base diameter of the right circular cone 114*b* is larger than cone 114*a* in FIG. 1B due to the increased number of segments being actuated (thereby increasing the slant height).

If a middle link is actuated at the proximal end, e.g., $B_1$, in FIG. 1D, while all other links remain straight or stationary to one another, than only the corresponding middle link at the distal end, $B_2$, will be manipulated and may be rotated to form, e.g., a cone with curved sides 116*a*. Or, as shown in FIG. 1E, a larger cone with curved sides 116*b* may be formed by manipulating the distal-most link, $A_1$, so that all proximal links bend into a curve. All links at the distal end will then mimic the curve, in an inverted fashion.

Although rotational movements are depicted in FIGS. 1B-1E, again, other complex, 3-dimensional movements incorporating up, down, right, left, and oblique movements, may also be accomplished. For example, FIG. 1F shows the distal end 120 of an articulating mechanism having multiple curvatures (122, 124, 126) along its length, each oriented in directions independent of one another. As noted, articulating mechanism 101 of FIG. 1F has nine pairs of links with three cable sets each providing for movement in 27 degrees of freedom, but other configurations of link pairs and cable sets will readily achieve similar complex movements and geometries. The ability of portions the mechanism to bend in different directions at the same time and create active complex configurations is provided by the independent actuation of each link or segment pair as controlled through its corresponding cable set.

The natural configuration of the segments, when connected by cable sets, is usually linear. Thus, if maintenance of a certain curvature or other complex configuration is desired at the distal end of the articulating mechanism, a malleable tube slidable over the proximal segments may be shaped to keep the proximal segments, and thus, their corresponding distal segments in a particular configuration. This may be advantageous where, for example, a surgeon has navigated the mechanism to a desired target location and wishes to "lock" the mechanism in place while e.g. actuating a tool associated with the mechanism, or engaging in a separate procedure altogether. By the term "malleable" it is meant that the tube is flexible enough so that it is capable of being shaped, but rigid enough so that it maintains its shaped form. In another variation, a locking rod may be inserted into one or more attachment channels extending through the links or segments to "lock" the proximal and distal segments of the articulating mechanism in place. The locking rod may be a malleable metal bar that may be shaped and then inserted into the attachment channels to set the proximal and distal segments into a particular configuration, or the locking rods may be provided in preshaped forms.

Other methods of freezing or locking the articulating-mechanism in place include the general use of links configured with ball-and-socket type joints together with a tensioning cable. Examples of such systems are generally described in e.g. U.S. Pat. No. 5,899,425 to Corey, Jr. et al. In such systems, a cable passing through the joints is tensioned, causing the balls and sockets to lock together frictionally. The cable can be tensioned by number of ways, including e.g. by affixing the end of the tensioning cable to a screw that is threaded into a nut affixed to the proximal end of the mechanism. FIGS. 3D and 3E illustrate ball-and-socket type link systems for use in articulating mechanisms of the invention. As shown, in FIG. 3D, each link 300 has a recessed socket 301 for receiving a spherical element or ball 302 disposed between the links. When a tension force is applied linearly along the axis of the links, the links will lock into place due to frictional forces between the balls and sockets. FIG. 3E shows a link system of similar configuration, with each link 310 and ball 312 having aligned channels 313 and 314 for the passage of a tensioning cable.

The articulating mechanism may be employed for remote manipulation of surgical instruments, diagnostic tools, various catheters, and the like, into hollow or chambered organs and/or tissues including, but not limited to, blood vessels (including intracranial vessels, large vessels, peripheral vessels, coronary arteries, aneurysms), the heart, esophagus, stomach, intestines, bladder, ureters, fallopian tubes, ducts such as bile ducts, and large and small airways. The articulating mechanism may also be used to remotely direct surgical instruments, diagnostic tools, various catheters, and the like, to solid organs or tissues including, but not limited to, skin, muscle, fat, brain, liver, kidneys, spleen, and benign or malignant tumors. The articulating mechanism may be used in mammalian subjects, including humans (mammals include, but are not limited to, primates, farm animals, sport animals, cats, dogs, rabbits, mice, and rats).

The articulating mechanisms may generally be used in any application or incorporated into other devices in which there is a user interface proximally, and an actuating element distally. The user interface may include the proximal end of an articulating mechanism, while the distal end may be attached to the actuating element. For example, in FIG. 6A, a remotely maneuverable surgical clamp 600 is shown. The clamp jaws 602 are attached to the distal end 604 of the articulating mechanism. The proximal end 606 is built into the clamp handle 608. A user is able to remotely position the clamp jaws 602 by manipulating the proximal end 606 of the articulating mechanism. A middle portion ("neck") 610 is also provided with the surgical instrument, the length and flexibility of which will vary with the application, with the neck providing the function of the spacer element. FIG. 6C shows another variation, where clamp handle 632 of surgical clamp 630 extends from proximal end 634. In other variations, the clamp jaws 602 may be exchanged for scissors or other cutting element, a dissector, a tissue grasper or needle grasper, a stapling device, a cauterizing or ablation device, and or other like tool or instrument.

In a further variation, the articulating mechanism itself may form the clamp jaws. In FIG. 6B, the clamp 612 has a user end with the proximal segments 614 extending from pivot 616 of the clamp. The cables that originate in the proximal segments 614 bifurcate into two cables each in the area of the pivot 616 so that each cable in the proximal end may then terminate in two separate articulating mechanisms that form opposing clamp jaws 618, 618. Thus, when a user manipulates the proximal segments 614, the jaws 618 will remain aligned and be correspondingly remotely manipulated. If desired, the proximal segments 614 may extend and be manipulated from one of the handles 620 of the clamp. The jaws can further be configured with particular tissue engaging surfaces, as well as ablation elements.

In yet a further variation, the articulating mechanism can be incorporated into a catheter and used to guide the catheter, e.g., in difficult central line placements, or in percutaneous or image-guided drainage catheter placement. As shown in FIG. 7, a catheter 700 may include an articulating mechanism with the proximal end of the mechanism 702 configured as an integral component of the user interface, in this instance, handle 706. The distal segments 708 form the distal portion of the catheter, and may be remotely maneuvered to guide the catheter 700 as it is advanced. In another variation (not shown), the articulating mechanism may be threaded through the catheter like a guidewire such that the proximal segments extend from the catheter proximal end, e.g., either directly from the catheter lumen, or from a bifurcated wye connector. The distal segments may extend from the catheter tip, and the catheter remotely guided to its target position as it is advanced. Typically, the articulating mechanism would then be removed to allow flow through the catheter. However, if the articulating mechanism that is employed has a central lumen, its removal may not be necessary.

In the same fashion, the articulating mechanism can be incorporated into and used to steer a flexible endoscope. In FIG. 8, endoscope 800 is configured such that the proximal end 806 of the articulating mechanism forms an integral part of the endoscope handle 804. The distal end 808 of the mechanism would constitute all or a part of the endoscope insertion tube 810. Upon manipulation of the proximal segments 806, the insertion tube 810 may be remotely manipulated.

In another variation, as shown in FIGS. 9A and 9B, the articulating mechanism could be used as a hand-held or self-retaining retractor 900. The proximal segments 902 and distal segments 904 may extend from the retractor handle 906 Manipulation of the proximal segments 902 will move the distal segments 904 in a reciprocal fashion. The distal segments can be manipulated to form a variety of complex shapes, the desired shape depending on the particular application. In operation, the distal end can be first positioned into the desired shape and then engaged with the target tissue. Alternatively, tissue retraction can be performed concurrently with manipulation of the distal end, i.e., the distal end can be engaged with the target tissue and through the act of manipulating the distal end, the tissue can be retracted.

A retractor typically must maintain its shape in use. Thus, the retractor may be "locked" into place using e.g. methods previously described. For example, the mechanism can include links with a ball and socket configuration together with a locking cable (not shown). Alternatively, a malleable sheath (not shown) may be placed over the proximal segments 902 prior to their manipulation or a locking rod (not shown) may be used to fix the retractor in a particular configuration, as has been previously described. In FIG. 9A, the retractor 900 is "u" shaped. In FIG. 9B, the retractor 900 has a triangular retracting surface. As noted, a retractor shape may be varied, depending on factors such as anatomical structure involved or type of surgical procedure.

In another variation, a number of articulating mechanisms can be combined to such a way that a user's finger movements can be remotely mimicked. For example, proximal ends of the mechanisms can be affixed to a user's fingers, for example, either strapped to each digit or otherwise secured to a glove that the user can wear. The distal ends will then move according to the user's finger movements. In the variation shown in FIG. 9C, mechanism 950 includes three articulating mechanisms operable by movement of a user's thumb, index, and middle fingers. As can be seen, proximal ends 951, 952 and 953 are affixed to a user's thumb, index finger and middle finger, respectively, by straps 957. The mechanism is further secured to the user's hand by strap 958 which secures the proximal end of spacer element 956 to the user's wrist. Movement of the user's thumb, index finger, and middle finger causes corresponding movement of distal ends 961, 962 and 963, respectively. Such variations may be advantageous in various surgical situations where gross manipulation of tissue or organs is required. In this as well as other variations, a protective pliable sheath can be extended over the mechanism to avoid potential damage to tissue from individual links or cables.

In yet another variation, the articulating mechanism may be used for the endoscopic treatment of atrial fibrillation. In particular, the articulating mechanism of the invention can be adapted to facilitate the creation of ablative lesions in heart tissue, which has been demonstrated to be effective in treating atrial fibrillation, as described e.g. by Cox, J. L. (2000). "Minimally Invasive Maze-III Procedure," *Operative Techniques in Thoracic and Cardiovascular Surgery* Vol. 5(1):79-92; Simha et al. (2001). "The Electrocautery Maze—How I Do It," *The Heart Surgery Forum* Vol. 4(4):340-345; and Prasad et al. (2001). "Epicardial Ablation on the Beating Heart; Progress Towards an Off-Pump Maze Procedure," *The Heart Surgery Forum* Vol. 5(2): 100-104; and as described in U.S. Pat. No. 6,161,543 to Cox et al. Such procedures can include epicardial or endocardial ablation, and many such procedures require accessing the posterior of the patient's heart, which can be difficult. The articulating mechanism of the invention can be configured with an ablative element, and together with its ability to form complex geometries; the mechanism can be readily navigated through the surrounding anatomy of the heart and easily positioned at various locations in or on the posterior of the heart to facilitate such ablation therapy.

Articulating mechanism 131 shown in FIG. 12A includes ablative element 125 connected to an electromagnetic energy source (not shown), such as an energy source which generated energy in radiofrequency (RF) or microwave frequency ranges. Such ablative elements are well known in the art, including those generally described in U.S. Pat. No. 6,471,696. The ablative element is mounted to links on the distal end 141 of the mechanism by way of attachment member 134 which is fittingly engaged with in channels 144 of links 142. The ablative element includes an insulated portion 127, typically formed of a thermoplastic elastomer, with longitudinally extending antenna or wire 129 for transmitting energy into tissue disposed therein. Other antenna or wire geometries, including helical coils, printed circuits, and the like are equally effective. Insulated conducting leads 136 and 137 are provided for connecting the energy source to the antenna or wire in a monopolar configuration. Bipolar configurations are also contemplated. Additional connectors 138 and 139 to the ablative element are also provided and can function in a variety of capacities, such as providing temperature or other sensors or probes, or to deliver a cooling medium to the element to cool the surrounding tissue and prevent extensive tissue damage, as is described, e.g., in U.S. Patent Application Publication No. U.S. 2003/0078644 to Phan.

FIG. 12B shows another variation of the articulating mechanism of the present invention configured for ablation. In this variation, articulating mechanism 133, which is configured for bipolar use, includes distal end 143 having distal links 152 that contain opposing electrodes 159. The opposing electrodes are separated by channel 164. Insulated conducting leads, such as leads 166 and 167, connect each pair of electrodes to the energy source (not shown). When energized, energy is transmitted across the electrode pairs, creating ablative lesions in the surrounding tissue. Again, additional connections 168 and 169 are also provided to provide additional functions, including probes, sensors, and cooling fluids.

While the above variations use ablative elements that rely on electromagnetic energy, articulating mechanisms according to the invention can also be readily adapted to incorporate other methods of ablation known in the art. For example, the ablative element could be a cryogenic or ultrasonic probe, or ablative elements that use laser energy, or other known ablative techniques.

Epicardial ablative lesions can be created as shown in the example depicted in FIGS. 13A-13F. Access to the posterior of a patient's heart 929 by articulating mechanism 131 may be initially made through, e.g., a thoracotomy, mini-thoracotomy, or trocar port (e.g., a 5-10 mm port), placed in the anterior chest wall of a patient. The spacer element (not shown) of the articulating mechanism may serve the purpose of a fulcrum at the port. As the surgeon bends the proximal links that are outside of the patient, the distal links inside the patient mimic the curvature of the outside links in a reciprocal fashion, in order to wrap around the superior vena cava 933 (13A) and continue to surround and the pulmonary veins 935 (13B) as the articulating mechanism is simultaneously advanced. Once in position, as shown in FIG. 13B, the ablative element on the distal end of the articulating mechanism can then be activated to create a lesion, and as depicted here in particular, pulmonary encircling lesion 943 (FIG. 13C). In FIGS. 13D and 13E the articulating mechanism is shown being repositioned to extend downward from the pulmonary veins 935 to create a lesion 939 down to the mitral valve annulus that connects to prior-formed pulmonary encircling lesion 943 (FIG. 13F).

The invention also contemplates kits for providing various articulating mechanisms and associated accessories. For example, kits containing articulating mechanisms having different lengths, different segment diameters, and/or different types of surgical instruments, or different types of locking rods or malleable coverings may be provided. The kits may be tailored for specific procedures, e.g., endoscopy, retraction, or catheter placement, and/or for particular patient populations, e.g., pediatric or adult.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

The invention claimed is:

1. A surgical instrument comprising:
   a proximal end and a distal end;
   a first linking member coupled to a user interface positioned near the proximal end;
   a second linking member coupled to a clamp tool positioned near the distal end;
   an elongate, rigid shaft extending between the first and second linking members;
   at least one cable set extending through the shaft and connected to the first linking member and to the second linking member such that movement of the first linking member causes corresponding movement in the second linking member; and
   an articulation locking mechanism configured to selectively lock the instrument in an articulated configuration,
   wherein the user interface comprises a handle having a first part connected to the first linking member and a second part pivotably connected to the first part, the user interface being configured to operate the clamp tool by pivoting the second handle part relative to the first handle part,
   wherein the first and second linking members each comprise a continuous flexible member having a plurality of flexible segments with flexible linkages positioned between adjacent segments, the segments further comprising a plurality of through lumens through which the cables movably pass; and
   wherein the instrument is configured such that movement of the handle relative to the shaft produces a proportionally scaled movement of the clamp tool relative to the shaft through the at least one cable set.

2. The surgical instrument of claim 1, wherein: the first linking member comprises a first set of links; the second linking member comprises a second set of links; and each link in the first set is connected to a corresponding link in the second set of links by a distinct cable set.

3. The surgical instrument of claim 1, wherein movement of the first linking member results in inverted movement of the second linking member.

4. The surgical instrument of claim 1, wherein movement of the first linking member results in movement of the second linking member in the same direction as the movement of the first linking member.

5. The surgical instrument of claim 1, wherein: the articulation locking mechanism comprises a ball and socket joint and wherein friction is exerted between the ball and socket to lock the instrument in an articulated configuration.

* * * * *

UNITED STATES PATENT AND TRADEMARK OFFICE
CERTIFICATE OF CORRECTION

PATENT NO. : 7,615,066 B2
APPLICATION NO. : 11/181445
DATED : November 10, 2009
INVENTOR(S) : Danitz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1003 days.

Signed and Sealed this

Nineteenth Day of October, 2010

David J. Kappos
*Director of the United States Patent and Trademark Office*